United States Patent
Joseph et al.

(10) Patent No.: US 10,739,239 B1
(45) Date of Patent: Aug. 11, 2020

(54) ROTATING MAGNETIC DISC MEDICAL ANALYZER AND COAGULATION PROFILER

(71) Applicant: iFirst Medical Technologies, Inc., Honolulu, HI (US)

(72) Inventors: Luke B. Joseph, Honolulu, HI (US); Thomas A. Hasling, Honolulu, HI (US)

(73) Assignee: iFirst Medical Technologies, Inc., Honolulu, HI (US)

( * ) Notice: Subject to any disclaimer, the term of this patent is extended or adjusted under 35 U.S.C. 154(b) by 0 days.

(21) Appl. No.: 15/638,156

(22) Filed: Jun. 29, 2017

Related U.S. Application Data

(63) Continuation of application No. 15/380,856, filed on Dec. 15, 2016, now abandoned, which is a continuation of application No. 14/526,057, filed on Oct. 28, 2014, now abandoned.

(60) Provisional application No. 61/896,405, filed on Oct. 28, 2013.

(51) Int. Cl.
  *G01N 33/86* (2006.01)
  *G01N 11/14* (2006.01)

(52) U.S. Cl.
  CPC ........ *G01N 11/14* (2013.01); *G01N 2011/147* (2013.01)

(58) Field of Classification Search
  CPC ................................................ G01N 33/86
  USPC .............................................. 422/73; 436/69
  See application file for complete search history.

(56) References Cited

U.S. PATENT DOCUMENTS

| | | | | |
|---|---|---|---|---|
| 3,053,078 A | * | 9/1962 | Jewett | G01N 11/14 73/53.01 |
| 3,520,659 A | * | 7/1970 | Steinberg | G01N 33/4905 310/86 |
| 3,650,698 A | * | 3/1972 | Adler | B01F 13/0809 210/222 |
| 3,695,842 A | * | 10/1972 | Mintz | G01N 33/4905 219/433 |

(Continued)

OTHER PUBLICATIONS

Shore-Lesserson, L. et al, Anesthesia & Analgesia 1999, 88, 312-319.*

(Continued)

*Primary Examiner* — Arlen Soderquist
(74) *Attorney, Agent, or Firm* — Knobbe, Martens, Olson & Bear LLP

(57) ABSTRACT

A medical analyzer and coagulation profiler performs various interrogations on specimens. A motor with reduction gearing moves and a video camera observes the samples, the cartridges or parts thereof. Changes in images are compared and recorded with a central processor that controls a display. Power supply, temperature controller, motor and gearing are mounted in a box which attaches to a smartphone. The smartphone provides the video camera, illumination and central processor that control the movement, temperature and display. The device makes testing simpler for small hospitals, clinics, ambulances, remote locations and individuals and controls a number of parallel or serial devices operating simultaneously or sequentially. A cartridge insertion actuates a circular motion to generate a blood profile based on changes. Change is analyzed with a video camera and processor such as in a smartphone and is plotted to show an amplitude and time. A smartphone provides a specific movement pattern.

16 Claims, 24 Drawing Sheets

(56) References Cited

U.S. PATENT DOCUMENTS

| | | | | |
|---|---|---|---|---|
| 3,704,099 A * | 11/1972 | Sanz | G04F 8/006 | 422/73 |
| 3,836,333 A * | 9/1974 | Mintz | G01N 33/4905 | 422/73 |
| 3,861,197 A * | 1/1975 | Adler | G01N 11/14 | 356/426 |
| 3,875,791 A * | 4/1975 | Fitzgerald | G01N 11/14 | 73/54.31 |
| 4,081,242 A * | 3/1978 | Girolami | G01N 33/4905 | 422/44 |
| 4,148,216 A * | 4/1979 | Do | G01N 33/4905 | 73/54.26 |
| 4,193,293 A * | 3/1980 | Cavallari | G01N 33/4905 | 73/54.41 |
| 4,317,363 A * | 3/1982 | Shen | G01N 11/10 | 73/64.41 |
| 4,328,701 A * | 5/1982 | Mau-Tung | G01N 33/4905 | 73/54.26 |
| 4,334,424 A * | 6/1982 | Kepes | G01N 11/14 | 73/54.28 |
| 4,341,111 A * | 7/1982 | Husar | G01N 33/4905 | 73/64.42 |
| 4,918,984 A * | 4/1990 | Martinoli | B01F 11/0082 | 73/64.43 |
| 4,964,728 A * | 10/1990 | Kloth | B01F 13/0818 | 356/427 |
| 5,016,469 A * | 5/1991 | Henderson | G01N 11/16 | 73/64.42 |
| 5,071,247 A * | 12/1991 | Markosian | G01N 21/82 | 250/214 L |
| 5,110,727 A * | 5/1992 | Oberhardt | B01F 11/0045 | 422/110 |
| 5,138,872 A * | 8/1992 | Henderson | G01N 11/16 | 73/64.41 |
| 5,154,082 A * | 10/1992 | Mintz | G01N 33/4905 | 422/73 |
| 5,163,317 A * | 11/1992 | Ono | G01N 11/142 | 73/54.32 |
| 5,223,227 A * | 6/1993 | Zuckerman | G01N 11/162 | 422/547 |
| 5,350,676 A * | 9/1994 | Oberhardt | B01L 3/502 | 356/39 |
| 5,523,238 A * | 6/1996 | Varon | G01N 33/4905 | 422/555 |
| 5,629,209 A * | 5/1997 | Braun, Sr. | G01N 11/105 | 422/547 |
| 5,777,215 A * | 7/1998 | Calatzis | G01N 33/4905 | 356/39 |
| 5,789,664 A * | 8/1998 | Neel | G01N 11/06 | 356/39 |
| 6,016,712 A * | 1/2000 | Warden | G01N 33/4905 | 73/864.21 |
| 6,103,196 A * | 8/2000 | Yassinzadeh | G01N 11/04 | 422/130 |
| 6,136,271 A * | 10/2000 | Lorincz | G01N 33/4905 | 422/73 |
| 6,165,795 A * | 12/2000 | Mize | G01N 33/4905 | 356/39 |
| 6,225,126 B1 * | 5/2001 | Cohen | G01N 11/162 | 422/73 |
| 6,573,104 B2 * | 6/2003 | Carr, Jr. | G01N 33/4905 | 422/49 |
| 6,586,259 B1 * | 7/2003 | Mahan | G01N 33/56972 | 435/7.1 |
| 6,591,663 B1 * | 7/2003 | Murray | A61B 10/0012 | 73/54.22 |
| 6,613,573 B1 * | 9/2003 | Cohen | G01N 11/162 | 422/73 |
| 6,898,532 B1 * | 5/2005 | Toh | G01N 33/4905 | 702/19 |
| 7,179,652 B2 * | 2/2007 | Cohen | G01N 11/162 | 422/73 |
| 7,182,913 B2 * | 2/2007 | Cohen | G01N 11/162 | 422/73 |
| 7,211,438 B2 * | 5/2007 | Toh | G01N 33/86 | 422/73 |
| 7,235,213 B2 * | 6/2007 | Mpock | C12Q 1/56 | 356/246 |
| 7,262,059 B2 * | 8/2007 | Zheng | B01F 7/26 | 422/73 |
| 7,399,637 B2 * | 7/2008 | Wright | G01N 11/14 | 422/430 |
| 7,422,905 B2 * | 9/2008 | Clague | G01N 11/14 | 422/430 |
| 7,439,069 B2 * | 10/2008 | Nippoldt | G01N 33/4905 | 422/561 |
| 7,524,670 B2 * | 4/2009 | Cohen | C12Q 1/56 | 435/287.1 |
| 7,732,213 B2 * | 6/2010 | Cohen | G01N 33/86 | 422/73 |
| 7,754,489 B2 * | 7/2010 | Cohen | G01N 33/86 | 435/13 |
| 8,076,144 B2 * | 12/2011 | Cohen | G01N 33/86 | 422/73 |
| 8,322,195 B2 * | 12/2012 | Glauner | G01N 33/4905 | 73/54.33 |
| 8,365,582 B2 * | 2/2013 | Sakai | G01N 11/14 | 73/54.31 |
| 8,383,045 B2 * | 2/2013 | Schubert | G01N 33/4905 | 422/73 |
| 8,448,499 B2 * | 5/2013 | Schubert | G01N 11/14 | 356/39 |
| 8,450,078 B2 * | 5/2013 | Dennis | G01N 21/17 | 435/13 |
| 8,795,210 B2 * | 8/2014 | Talish | A61H 1/005 | 36/141 |
| 8,877,710 B2 * | 11/2014 | Johansson | A61K 31/557 | 514/13.5 |
| 9,046,512 B2 * | 6/2015 | Djennati | G01N 11/14 | |
| 9,063,161 B2 * | 6/2015 | Dennis | G01N 21/17 | |
| 10,184,872 B2 * | 1/2019 | Sakai | G01N 11/14 | |
| 2002/0168294 A1 * | 11/2002 | Carr, Jr. | G01N 33/4905 | 422/73 |
| 2003/0064505 A1 * | 4/2003 | Harttig | G01N 33/4905 | 435/287.1 |
| 2003/0069702 A1 * | 4/2003 | Cohen | G01N 11/162 | 702/23 |
| 2003/0073244 A1 * | 4/2003 | Cohen | G01N 33/86 | 436/69 |
| 2003/0180824 A1 * | 9/2003 | Mpock | C12Q 1/56 | 435/13 |
| 2003/0199428 A1 * | 10/2003 | Carr, Jr. | C12Q 1/56 | 435/13 |
| 2004/0131500 A1 * | 7/2004 | Chow | G01N 11/14 | 422/72 |
| 2004/0203163 A1 * | 10/2004 | Cohen | G01N 33/86 | 436/69 |
| 2004/0224419 A1 * | 11/2004 | Zheng | B01F 7/26 | 436/69 |
| 2005/0180886 A1 * | 8/2005 | Bote Bote | G01N 33/4905 | 422/73 |
| 2005/0233460 A1 * | 10/2005 | Clague | G01N 11/14 | 436/69 |
| 2005/0233466 A1 * | 10/2005 | Wright | G01N 11/14 | 436/165 |
| 2005/0255601 A1 * | 11/2005 | Nippoldt | G01N 33/4905 | 436/69 |
| 2006/0034734 A1 * | 2/2006 | Schubert | G01N 33/4905 | 422/430 |
| 2007/0059840 A1 * | 3/2007 | Cohen | G01N 33/4905 | 436/69 |
| 2007/0158246 A1 * | 7/2007 | Davies | G01N 33/4905 | 210/85 |
| 2007/0184508 A1 * | 8/2007 | Cohen | G01N 33/86 | 435/11 |
| 2008/0015477 A1 * | 1/2008 | Talish | A61H 1/005 | 601/79 |

(56) References Cited

U.S. PATENT DOCUMENTS

| | | | | |
|---|---|---|---|---|
| 2008/0038828 | A1* | 2/2008 | Cohen | G01N 33/86 436/69 |
| 2008/0206880 | A9* | 8/2008 | Clague | G01N 11/14 436/69 |
| 2008/0233554 | A1* | 9/2008 | Sehgal | A01N 1/0215 435/2 |
| 2008/0261261 | A1* | 10/2008 | Grimes | G01N 33/4905 435/29 |
| 2009/0198120 | A1* | 8/2009 | Gurbel | G01N 33/86 600/369 |
| 2009/0304547 | A1* | 12/2009 | Werner | A61B 5/14532 422/400 |
| 2010/0139375 | A1* | 6/2010 | Johns | G01N 11/08 73/54.24 |
| 2010/0154520 | A1* | 6/2010 | Schubert | G01N 11/14 73/54.28 |
| 2010/0170327 | A1* | 7/2010 | Glauner | G01N 33/4905 73/54.41 |
| 2010/0184201 | A1* | 7/2010 | Schubert | G01N 33/4905 435/287.1 |
| 2010/0268094 | A1* | 10/2010 | Hasling | A61B 5/02416 600/484 |
| 2011/0036150 | A1* | 2/2011 | Sakai | G01N 11/14 73/54.31 |
| 2011/0151491 | A1* | 6/2011 | Dennis | G01N 21/17 435/13 |
| 2011/0223663 | A1* | 9/2011 | Sehgal | A01N 1/02 435/374 |
| 2011/0268732 | A1* | 11/2011 | Johansson | A61K 31/557 424/133.1 |
| 2012/0028342 | A1* | 2/2012 | Ismagilov | B01L 3/502738 435/283.1 |
| 2012/0294767 | A1* | 11/2012 | Viola | G01N 29/024 422/73 |
| 2013/0195722 | A1* | 8/2013 | Mitchell | G01N 11/14 422/82.05 |
| 2013/0267017 | A1* | 10/2013 | Dennis | G01N 21/17 435/288.7 |
| 2014/0020475 | A1* | 1/2014 | Inoue | A61B 5/0053 73/788 |
| 2014/0047903 | A1* | 2/2014 | Sakai | G01N 11/14 73/54.28 |
| 2014/0273249 | A1* | 9/2014 | Yuan | G01N 33/86 436/69 |
| 2015/0024473 | A1* | 1/2015 | Wu | G01N 27/74 435/287.1 |
| 2015/0118691 | A1* | 4/2015 | De Laat | C12Q 1/56 435/7.4 |
| 2015/0226725 | A1* | 8/2015 | Gill | G01N 33/49 73/64.41 |
| 2015/0253343 | A1* | 9/2015 | Pearce | G01N 33/86 436/501 |
| 2015/0305681 | A1* | 10/2015 | Nadkarni | A61B 5/7246 600/369 |

OTHER PUBLICATIONS

Muller, O. et al, Macromolecues 1991, 24, 3111-3120.*
Gasull, A. et al, IEEE 1992, 1948-1949.*
Ziemann, F. et al, Biophysical Journal 1994, 66, 2210-2216.*
Crocker, J. C. et al, Journal of Colloid and Interface Science 1996, 179, 298-310.*
Smith, Z. J. et al, PLOS One 2011, 11, paper e17150, 11 pages.*
Hortschitz, W. et al, IEEE Sensors Journal 2011, 11, 2805-2812.*
Castro-Palacio, J. C. et al, American Journal of Physics 2013, 81, 472-475.*
"GPU-accelerated video processing on Mac and iOS", Sunset Lake Software, www.sunsetlakessoftware.com/2010/10/22/gpu-accelerated-video-processing-mak-and-iOS; Oct. 22, 2010.

* cited by examiner

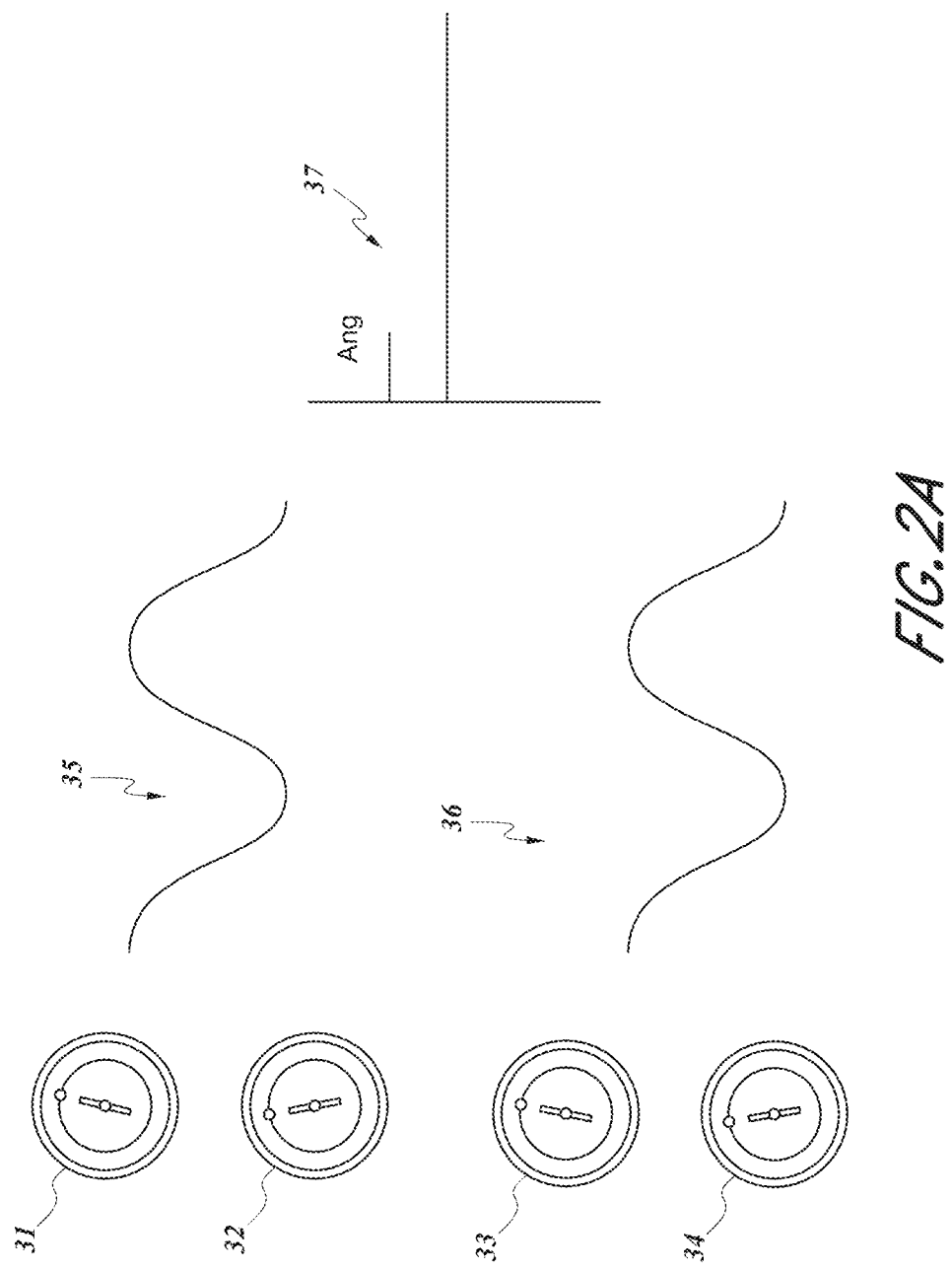

ROTATING MAGNETIC DISC MEDICAL ANALYZER AND COAGULATION PROFILER

This application claims the benefit as a continuation of U.S. patent application Ser. No. 15/380,856 filed on Dec. 15, 2016, which is in turn a continuation of U.S. patent application Ser. No. 14/526,057 filed on Oct. 28, 2014, which is a nonprovisional of U.S. Provisional Application No. 61/896,405 filed Oct. 28, 2013, each of the foregoing of which are hereby incorporated by reference in their entireties as if fully set forth herein. This application claims the benefit of U.S. Provisional Application No. 61/896,405 filed Oct. 28, 2013, which is hereby incorporated by reference in its entirety as if fully set forth herein.

This invention was made with government support under Contract No. W81XWH-11-C-0055 awarded by the U.S. Army Medical Research Acquisition Activity. The government has certain rights in the invention.

BACKGROUND OF THE INVENTION

Five million people around the world die of trauma on an annual basis. Up to 20% of these deaths are preventable with better control bleeding. In these types of traumatic injury, the incidences of coagulation abnormalities are high. For example, natural supplies of proteins such as Factor VII are quickly depleted after trauma, which can quickly lead to hemorrhage-related death. Detecting these abnormalities quickly after the trauma often can be a predictor of the patient's mortality. These diagnostics can be a decision aid for providers and provide feedback for lifesaving actions, such as transfusions.

Although techniques such as prothrombin time (PT) and partial thromboplastin time (PTT) can test coagulation, only the first state of coagulation and plasma hemostasis are tested rather than coagulocompetence. In addition it has been shown that PT and PTT tests do not predict coagulation abnormalities as effectively as coagulation profiles, such as thrombelastography (TEG) shown in FIG. 10A. In addition separating the plasma complicates the blood processing and adds steps to the coagulation initiation.

Other coagulation profiling techniques such as thrombelastography and rotational thromboelastometry (ROTEM) shown in FIG. 10B provide a more complete coagulation profile by using whole blood. The use of whole blood includes the role of platelets, blood factors and phospholipids in the coagulation cascade. Unfortunately both standard coagulation tests (PT, PTT, etc.), and newer systems such as TEG and ROTEM, require relatively large equipment, controlled conditions and trained technicians to perform tests. These limitations prevent these diagnostic tools from being at the point of injury (POI).

In order to most effectively treat traumatic injuries, it is critical to diagnose coagulation abnormalities at the POI, ideally by first responders such as paramedic and emergency medical technicians (EMT) (FIG. 9) Paramedics and EMTs could rapidly evaluate the coagulopathy and obtain guidance in using blood products or administration of coagulation related drugs. In addition, further integration of other coagulation relevant assays, such as complete blood count (CBC) or hematocrit (HTC), base deficit, platelet count, and PaO2 with a TEG-like profile could be an invaluable addition to point-of-care diagnostics.

Needs exist for improved base medical analyzers and coagulation profilers.

SUMMARY OF THE INVENTION

The invention solves the existing problems by providing new base medical analyzers and coagulation profilers that can be available to be quickly used.

An example of the invention is a new cartridge based biological microelectromechanical system (BioMEMS) that rotates back and forth in a circular motion in direct contact to a blood sample, while the blood coagulates. This rotation changes over time as the blood coagulates in the sample. The change in motion is analyzed through a video camera (in one case an iPhone camera) and then is plotted to show an amplitude over time. The plot of motion over time is indicative of particular forms of coagulation disorders. The rotating motion of the BioMEMS device is induced externally using a magnetic field. The rotation induced is not limited to a magnetic field but could be direct mechanical or electrostatic inducer of the rotation. The magnetic actuation is provided by a motor, servo or similar device that turns a magnet. The motor can be controlled mechanically or electronically, by the iPhone for example, to provide a specific pattern. In one case the pattern is 4° 45' in 5 seconds. There can be a large range of patterns, dependent on application. In one case the profile is measured for 30 to 60 minutes, however, time may vary depending on application.

Use of a mobile device, such as an iPhone and the new device has been demonstrated to show coagulation over time in the form of a coagulation profile. The invention makes the testing simpler by use of a cartridge and provides a method of having a large number of sequential tests to monitor a patient from POI to the emergency room (ER), operating room and recovery. The overall system and the cartridge are very small. The use of cartridges in the invention simplifies the process as compared to conventional techniques. Being small and portable there is potential provided by the invention for a large number of parallel or serial devices operating simultaneously.

The system comprises a handheld medical analyzer platform, which works with different disposable application cartridges to perform a variety of interrogations on specimen samples. One application includes attaching a biological microelectromechanical system (BioMEMS) cartridge that generates blood coagulation profiles indicative of particular forms of coagulation disorders. The device makes coagulopathy testing simpler for small hospitals, clinics, ambulances, remote locations and individuals by use of a cartridge and permits for a larger number of parallel or serial devices operating simultaneously. One insertion of a cartridge actuates an oscillating circular motion to generate a blood coagulation profile based on a change in rotational motion as blood coagulates in a sample. Change in rotational motion is analyzed through a video camera such as in a smartphone and is plotted to show an amplitude over time. Actuation of the BioMEMS can be achieved by magnetic actuation of a motor controlled by an iPhone or a smart phone to provide a specific rotational pattern.

A liquid coagulation measuring device has a case and a motor within the case. Gearing is connected to the motor. A magnet is connected to the gearing and is configured for magnetic coupling to a movable element within a liquid well. A temperature controller is connected to the case and is configured for controlling temperature of liquid in the liquid well.

A light source illuminates the movable element and a recorder records movement of the movable element. A compact microscope is configured for alignment with the liquid well and a video camera is aligned with the compact microscope.

An attachment on the case is configured for attaching to a smartphone having a video camera, a central processor and display. The attachment is configured for aligning the video camera with the liquid well and the movable object.

The case has a base and a cover. The base has a bottom, sides and a top and a space in the top for positioning and holding a smartphone. The cover is configured for covering border areas around a display face of the smartphone. The cover and the sides have complementary connections configured for holding the cover on the base and holding the smartphone within the case. One of the sides has an opening for receiving a cartridge with the well.

An elastomeric boot surrounds the case and is adapted for protecting the measuring device and the smartphone. The opening in the case is configured for receiving the cartridge. A passage flows the liquid into the well through a cartridge port outside of the opening into one of the sides of the case. Reduction gearing is connected to the motor. The reduction gearing is configured for reciprocating the magnet and thereby reciprocating the movable element. The reduction gearing is configured for rotatably reciprocating the magnet and thereby rotatably reciprocating the movable element.

A liquid coagulation measuring device has a case and a reciprocating motor within the case. Reduction gearing is connected to the motor. A contactless coupling is connected to the reduction gearing and is configured for reciprocating a movable object in a well within the case. A temperature controller controls temperature within the case. A compact microscope in the case is configured for magnifying an image of a movable object placed within the case.

A light source illuminates the liquid or the movable object placed within the case. A video camera records movement of the movable object placed within the case. A power source is connected to the motor, the light source and the video camera. A central processor is connected to the power source and to the video camera and records a time from start of movement of the movable object until a change of the movement.

A display is connected to the central processor. A smartphone connected to the case provides control of the light source, the video camera, the central processor and the display.

A rectangular box has a bottom, a top and sides connecting the bottom and the top, supporting the smartphone on the top. A cover has a large opening with a frame for exposing the display and a start button of the smartphone while holding the smartphone on the box. An opening in at least one of the sides receives a cartridge having the liquid well. A pusher is connected to the reduction gearing for pushing a lid on the cartridge and dropping the movable object into the well.

A measuring device is turned on. Internal temperature is controlled in the device. A cartridge is inserted into the device beneath a small microscope or a magnifier. A liquid sample is injected into a well within the cartridge. The well or a movable device therein is reciprocated. The movable device is illuminated and is observed through the microscope with a video camera. Times of changes in movement of the movable device are recorded. The movable device is reciprocated with a contactless magnetic coupling. Time differentiation is recorded between a start of movement of the movable device and slowing and stopping of movement of the movable device. The movable device is placed in the well after the injecting of the liquid sample. A power source is connected to the heat controller and the motor. The smartphone provides the illuminating and a video camera and a central processor for recording times of changes in movement of the movable device and creating displays according to the changes in movement of the movable device.

A smartphone connected to the measuring device is turned on to start the illuminating, the video camera and the central processor.

These and further and other objects and features of the invention are apparent in the disclosure, which includes the above and ongoing written specification, with the claims and the drawings.

BRIEF DESCRIPTION OF THE DRAWINGS

FIG. 2A are images describing translation of device motion into zero amplitude profile.

FIGS. 11A-15 show examples of cartridges.

FIGS. 11A and 11B are perspective and a schematic side view showing an example of a cartridge, platform, well, extended lid, an abutment on the platform and a disk attached to the lid, all of which are inserted in a receiver before fluid is injected into the well.

FIG. 14 is a perspective view of a cartridge without a lid showing a fluid injection port at one end of a passageway to the well and a retaining clip for retaining the cartridge in the receiver.

FIG. 15 shows a two-piece injection construction of the cartridge platform for compatibility with manufacture by injection molding.

DETAILED DESCRIPTION OF THE INVENTION

Figure 1A:
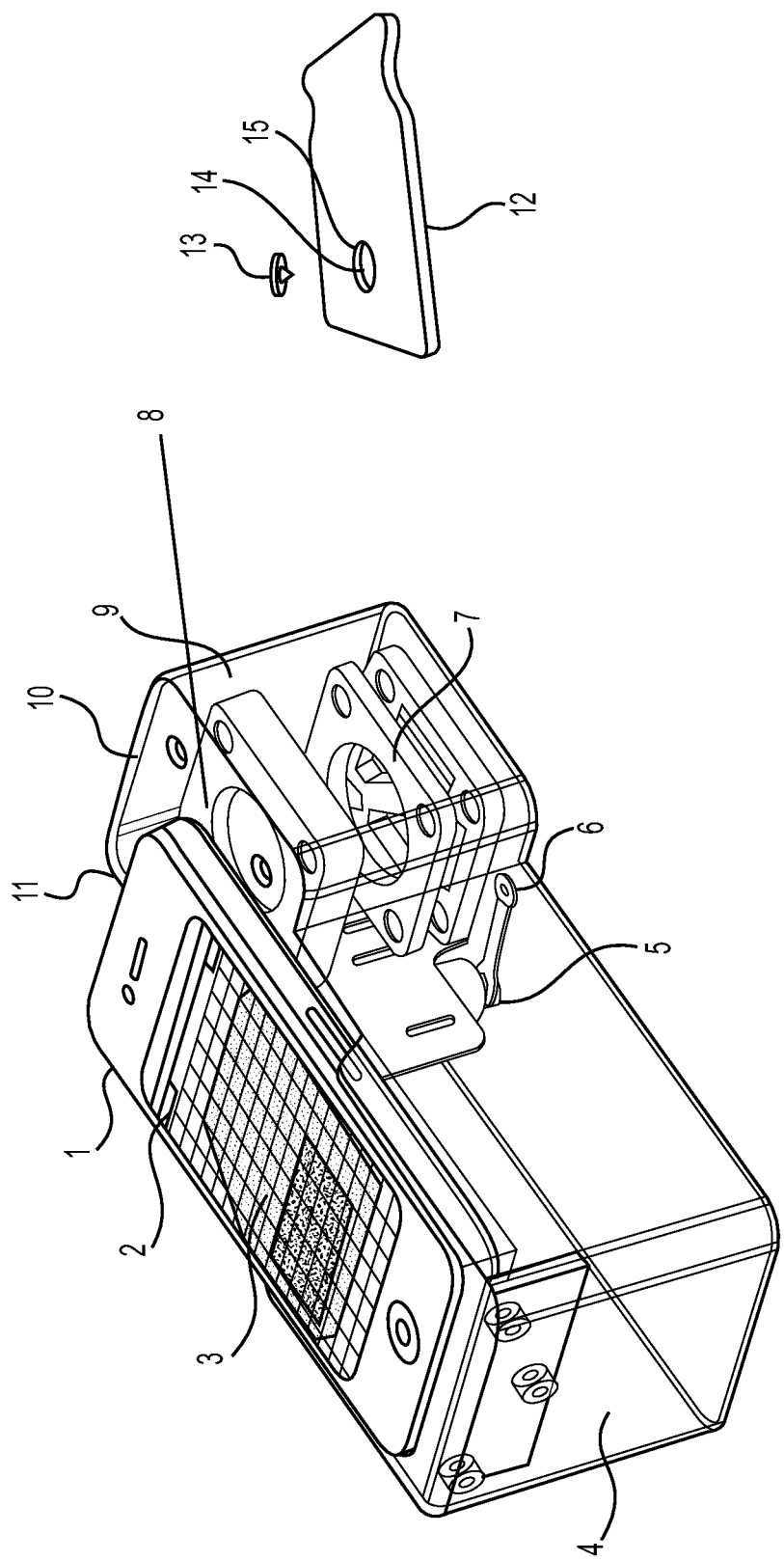
FIG. 1A is a CAD rendering of the new Coagulation Profiler and subsystems.

The invention provides a handheld medical analyzer platform and biological microelectromechanical systems (BioMEMS) cartridges. This combined system uses microfluidics, optics, a mobile device (e.g. a smartphone or tablet) and video analysis software to create a handheld analyzer that produces data used in medical and biological diagnostics. In this embodiment two primary components are the handheld medical analyzer and the coagulation profile cartridge. The combination of the handheld analyzer and coagulation profile cartridge provide results equal to bench top systems used in hospitals, such as TEG and ROTEM. The handheld medical analyzer is a platform that is capable of analyzing a variety of cartridges. However the coagulation profile cartridge is specific to coagulopathy applications only.

Although the cartridges are intended to be disposable, they also can be implemented in a permanent fashion when cleaned properly and constructed of the proper material. Combined, the handheld medical analyzer and coagulation profile cartridge produce a coagulation profile which is displayed and stored on the analyzer. In this embodiment of the invention, the cartridge provides data used in diagnosing different forms of coagulopathy.

Although the combination of the handheld analyzer and coagulation profile cartridge is one part of the invention, the handheld analyzer is not limited to analyzing this specific cartridge.

Other similar embodiments include profiling the coagulation of Limulus amebocyte lysate (LAL). In this case the extent of LAL coagulation would be representative of the presence of gram negative bacteria, since the LAL reacts with bacterial endotoxin or lipopolysaccharide (LPS).

A similar cartridge would also apply to other assays that detect a physical change in the sample, such a viscosity, elasticity or viscoelasticity. Examples of these embodiments may include saliva, cervical mucus or other body fluids.

Furthermore the handheld analyzer is also capable of using the same basic configuration to analyze a great many cartridges. These embodiments would also capture data using the video camera and interrogated using the CPU and GPU running proprietary software. These cartridges include, but are not limited to CBC, HTC, $PaO_2$, pH and blood type.

Likewise similar use of a smartphone for cartridge analysis is not limited to video input, but also could use many other sensors on the smartphone, including direct electrical signals, wireless signals, manometer, accelerometer, gyroscopes and compass. This includes combinations of the different methods of obtaining direct sensor information and indirect supplementary sensor information. An example of this would be using the combined system to provide a coagulation profile, while using the smartphone, wireless communication, accelerometers, gyroscopes, GPS, etc. to provide stabilization in rough environments such as a helicopter which is in motion and vibrating. These subsystems could also be used to send the coagulation profile, GPS coordinates to the ER providing an estimated time of arrival (ETA) and allowing for preparation of blood products, etc., in advanced for the patient's arrival.

A primary embodiment of the combined inventions is shown in FIG. 1A. The coagulation profile cartridge 12 is inserted into the cartridge slot 7 where the BioMEMS device motion interfaces with the sample 15 and the motion is captured using the smartphone 1 video camera 11 and is analyzed using the smartphone central processing unit (CPU), graphics processor unit (GPU) running proprietary software. The resultant coagulation profile 3 is displayed 2 on smartphone 1 (e.g. iPhone) screen along with the measured parameters, similar to TEG/ROTEM, Table 1, Table 2. A custom enclosure 4 provides a docking point for the smartphone and attachment of peripheral components. In this embodiment the peripheral components consist of a motor 5, mechanical linkage 6 and compact microscope assembly 8, light source 9 and temperature control unit 10. The motor and linkage can be replaced with a servo and gearing, to provide the desired rotational actuation.

The coagulation profile cartridge 12 is interrogated using the compact microscope 8 and video camera 11.

Figure 1B:
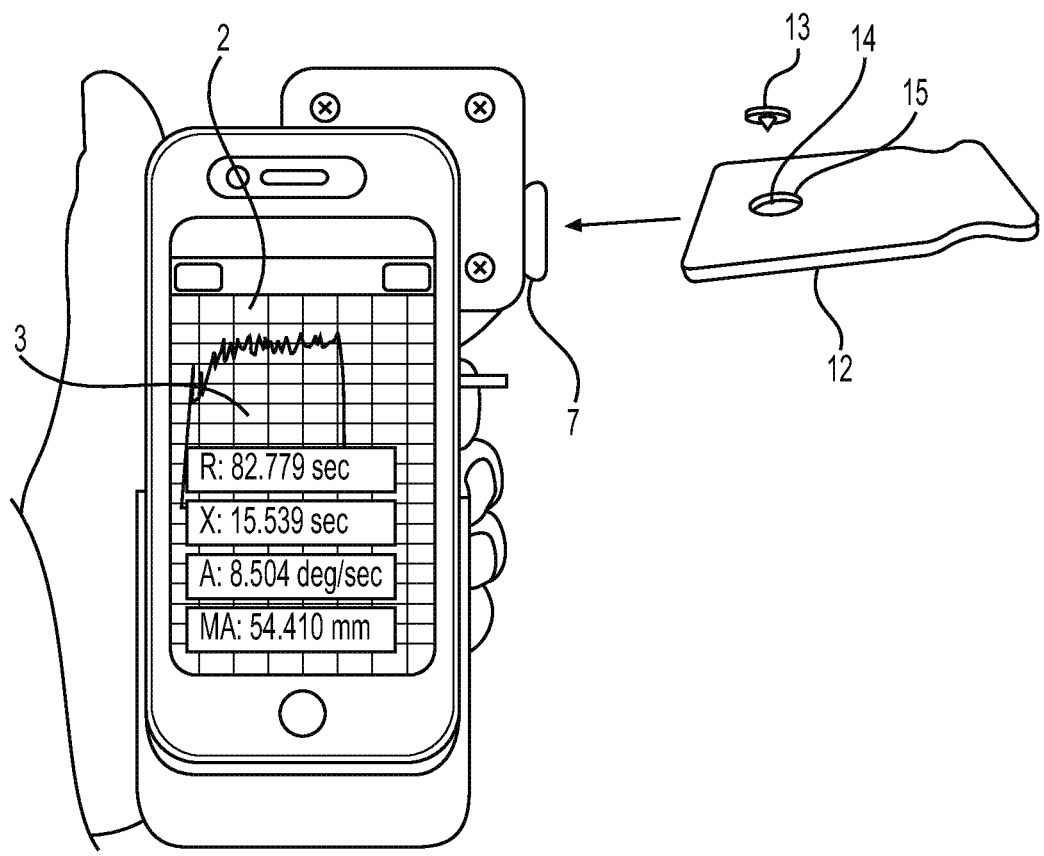
FIG. 1B is a prototype showing blood placed on cartridge is loaded into the analysis slot.

The loading protocol for the simplest embodiment of the combined system is: place blood 15 into well 14 on cartridge 12 and load the cartridge into analysis slot 7, also shown in FIG. 1B.

The disc 13 may be removed prior to filling the well 14, or the well may be filled with the disc in place. In this simple embodiment the well would be filled using a pipette.

Figure 1C:
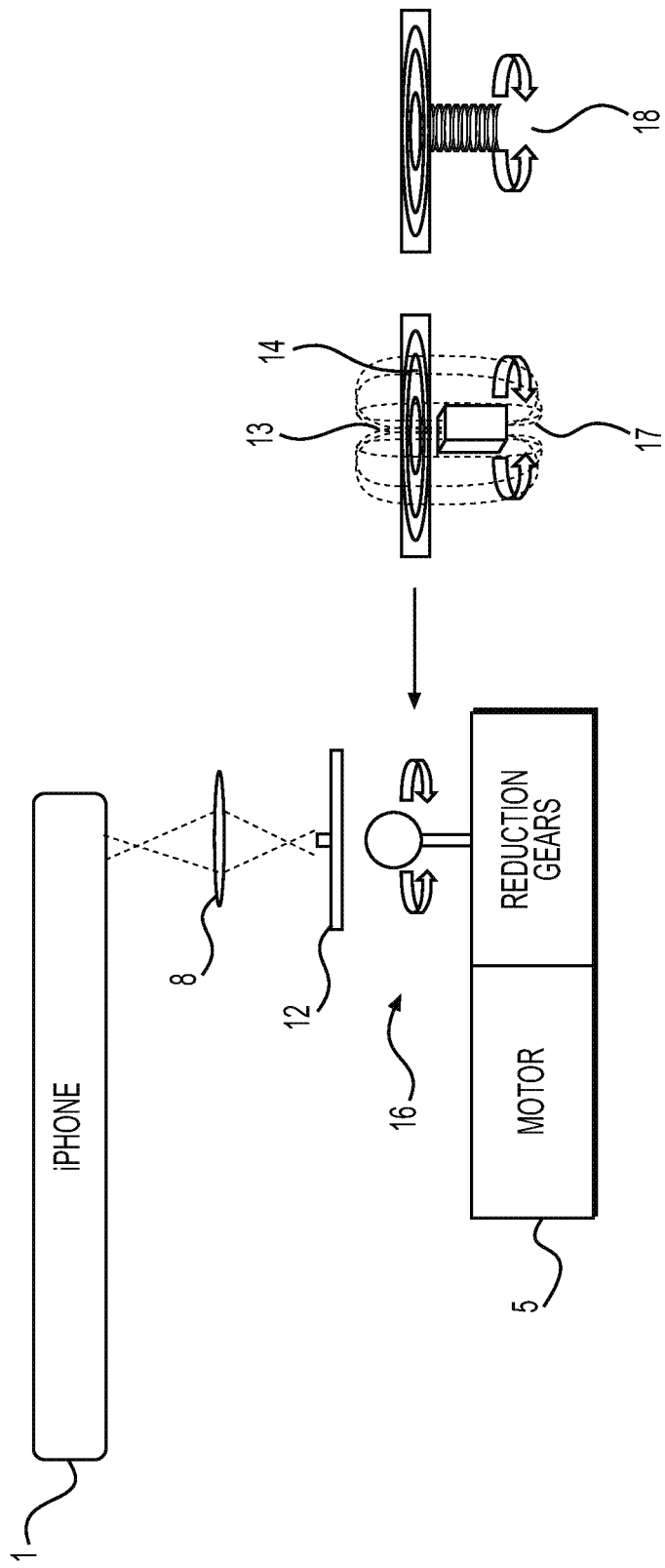
FIG. 1C is a conceptual rendering of cartridge actuation and sub system.

Upon loading the cartridge the measurement begins as the disc is actuated, as shown in FIG. 1C. Actuation in this embodiment is performed using a motor 5, mechanical linkage 6 in the form of reduction gears and magnet 16, which couples motion to the cartridge disc 13. Other embodiments would include electromagnetic induction or direct mechanical drive via a spring.

By embedding ferrous metal into the cartridge disc 13, the magnetic field 17 couples the disc with the magnet. This coupling forms a link analogous to a torsion spring 18. Motion is thereby induced into the disc by rotating the magnet. In this embodiment the rotation is ±4° 45' degrees over 10 seconds. Other embodiments would include any number variations in the angular rotation over time.

Figure 1D:
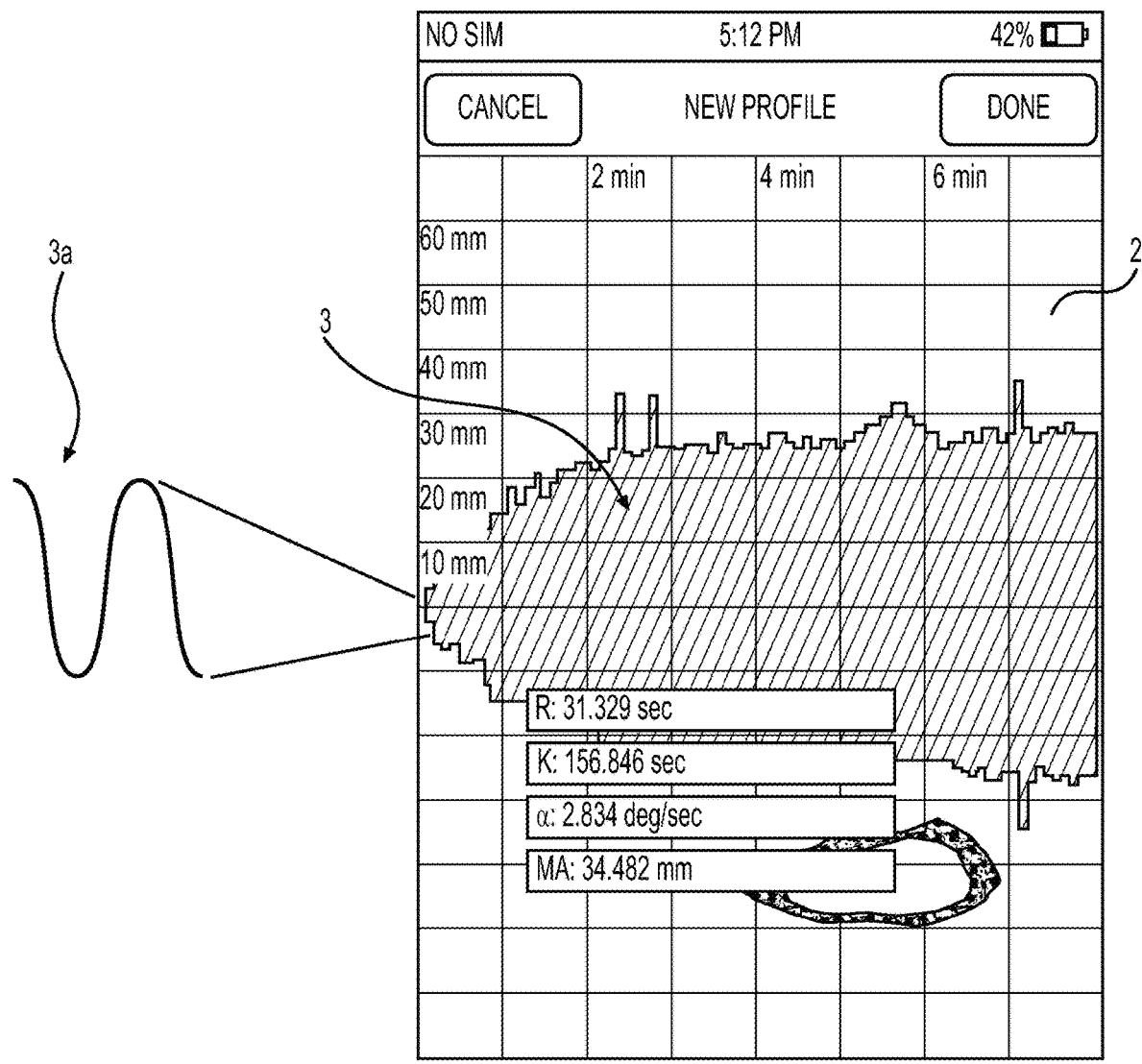
FIG. 1D is a description of displayed profile, relative to cartridge actuation.

In the embodiment the degree to which the motion is decoupled is representative of the displayed 2 profile 3, as shown in FIG. 1D. Both processed profiles 3 and preprocessed traces are sinusoidal waveforms, e.g. 3a, that represent the motion or decoupled motion. The sinusoidal waveform is acquired using the video camera and the CPU and GPU running proprietary software.

Figure 1E:
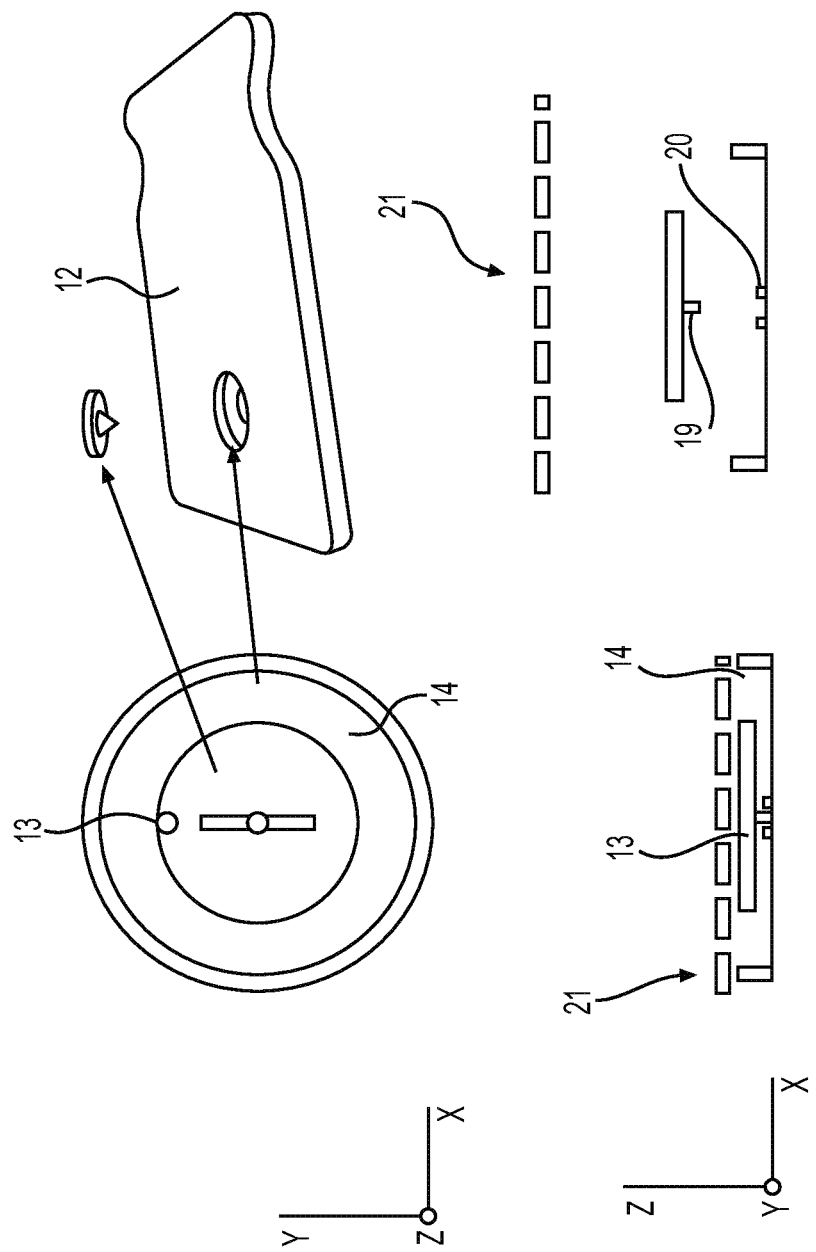
FIG. 1E is a detailed description of BioMEMS coagulation profile cartridge.

The alpha numeric displays:
R: 31.329 sec
K: 156.846 sec
a: 2.834 deg/sec
MA: 34.482 mm FIG. 1E shows a cartridge 12, an enlarged well top view, side cross section and an exploded side cross section. As shown in FIG. 1E, the cartridge has a well 14 and a disc 13. The disc is seated in the well via a spindle 19 and a bearing cup 20, at the bottom of the well. Both the well and the disc are sealed in the cartridge with a clear plastic lid 21. The lid can be hinged, sliding to allow sample insertion, or a microfluidic channel maybe used to load the sample into the well. This particular subcomponent of the cartridge may be realized in a number of different embodiments. These range from a simple hole in the lid to more complex automated microfluidics channels and chambers which meter the appropriate amount of blood or reagent into the well. Likewise the insertion of the sample may range from manually using a pipette to the use of automated microfluidics.

Figure 1F:
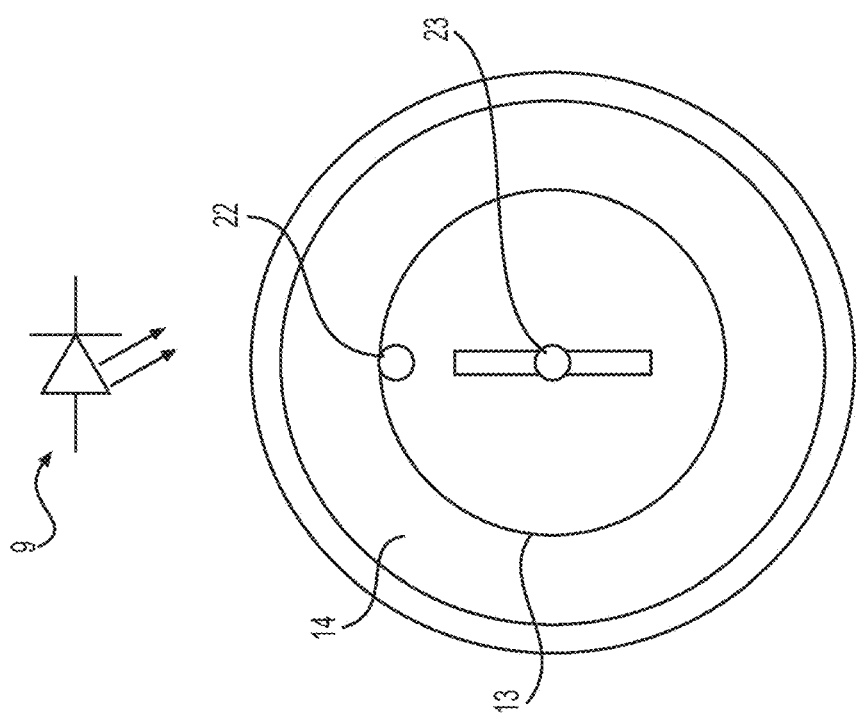
FIG. 1F is an image describing BioMEMS device marking relative to tracking.

The motion of the disc is captured by tracking two points overtime. FIG. 1F shows the pivot point 23 at the center of the disc 13 and a tracking point 22 at the outside edge of the disc. Each point is a unique color. In this embodiment the colors are florescent when illuminated using a UV LED light source 9. Both points are tracked by selecting the color to be tracked on the smartphone screen followed by selecting a threshold for the hues of the selected color to be included. The centroid of each of the prescribed points is then calculated to determine the exact location to be tracked. The angular motion is then calculated by comparing the centroid of the pivot point 23 to the centroid of the tracking point 22. This calculation is performed real-time and is used to calculate the displayed profile continuously over time.

Figure 2B:
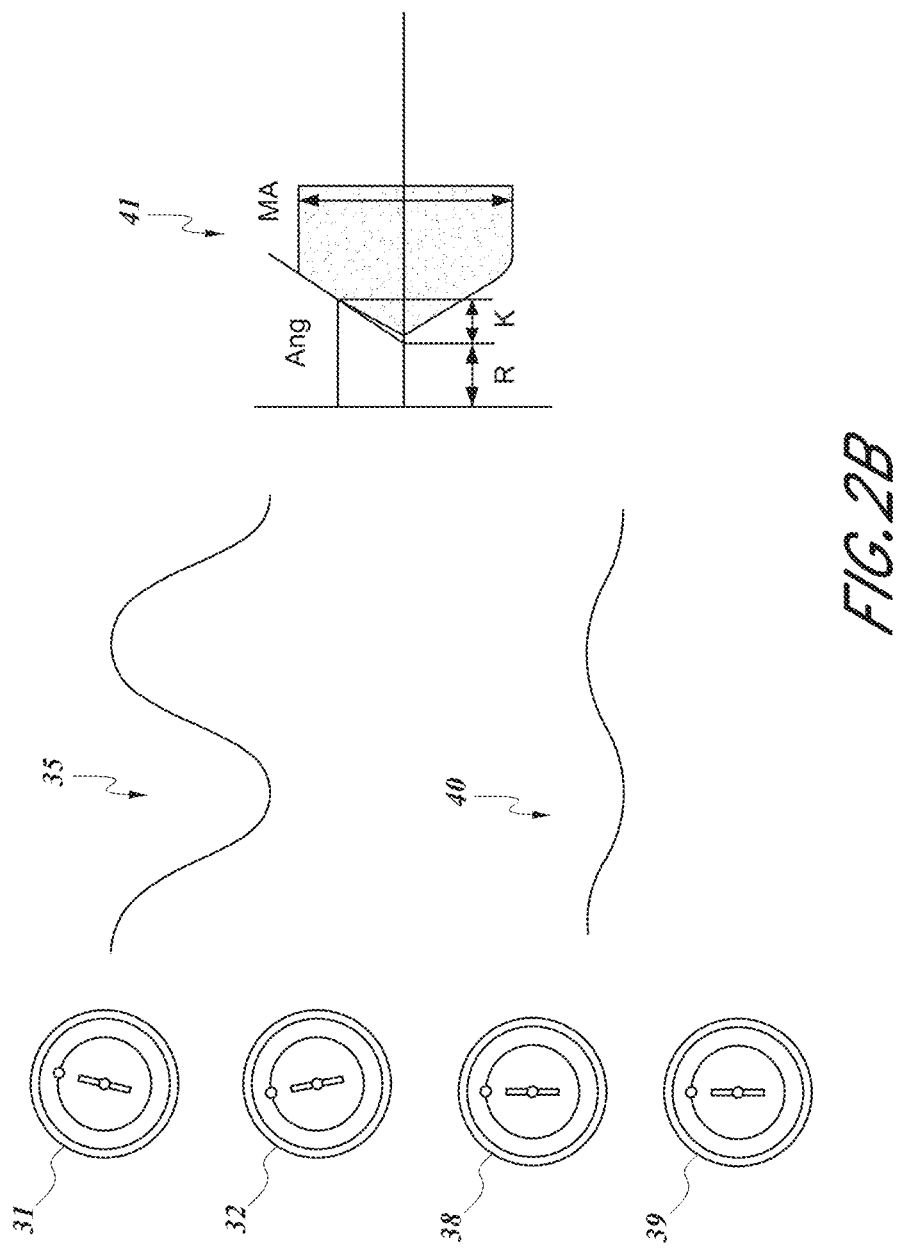
FIG. 2B are images describing translation of device motion into max amplitude (MA) profile.

The detailed translation of the device motion is shown in FIG. 2A. At the beginning of the measurement the disc motion is uninhibited and rotates the full range of motion, plus 4° 45' 31 and minus 4° 45' 32, in the fluid tested. This initial motion, before the onset of coagulation, is recorded as the baseline trace 35. The baseline trace is then differenced with the subsequent motion trace 36 to detect coagulation, which inhibits the coupling of motion of the magnet with the motion of the disc. In this embodiment, the displayed trace 37 (coagulation profile) is the difference between the baseline trace 35 and the subsequent motion trace 36. Prior to coagulation the baseline trace 35 is the same as the pre coagulation subsequent motion trace 36, and the coagulation profile 37 is the difference between the two: zero. As the blood coagulates, the induced motion is decoupled, and the magnetic field is no longer strong enough to overcome the viscoelasticity of the blood, as shown in FIG. 2B. Initially the motion is uninhibited 31, 32 producing the baseline motion 35. When coagulation occurs, decoupling reduces the induced motion 38, 39. Upon coagulation the large baseline trace 35 is differenced with the small post coagulation subsequent motion trace 40, resulting in a large amplitude profile 41. The moment in time shown, is at maximum amplitude represented by the parameter similar to the TEG parameter MA. As shown at the right of FIG. 2B and in FIG. 1B, the "reaction time" is the calculated time in decimal fractions of a second for a clot to reach 2 mm, "22 mm time" is the time in decimal fractions of a second for a clot to reach 22 mm, and "angle" is the slope of the angle between "reaction time" and 22 mm time. The "max clot" is maximum strength of a clot indicated in mm.

Figure 3:
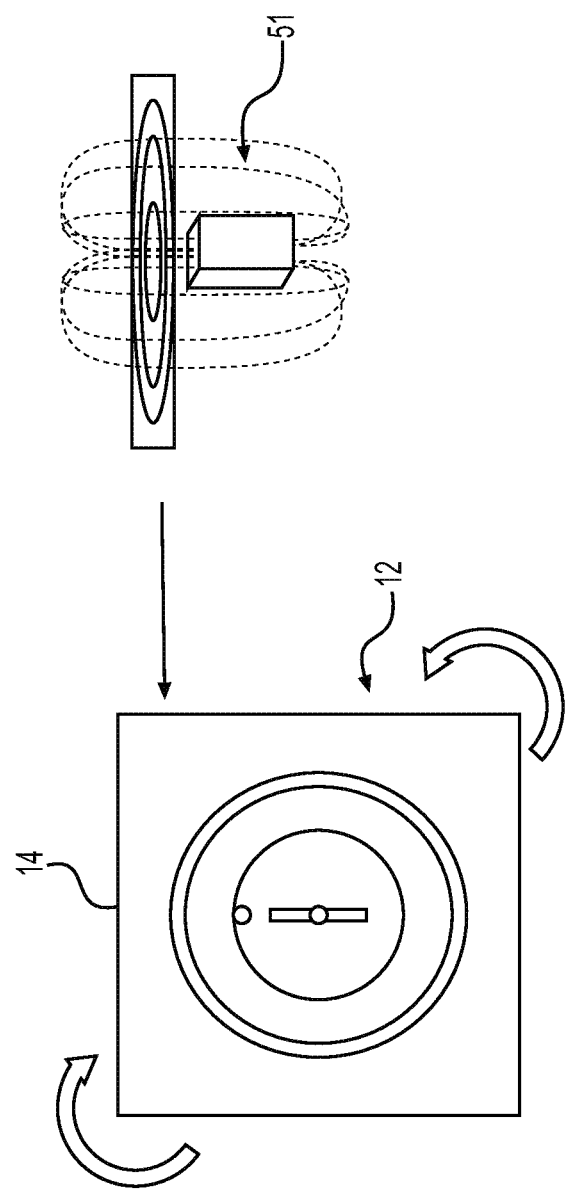
FIG. 3 shows an alternate embodiment with a fixed magnet.

A second embodiment of the BioMEMS device is shown in FIG. 3. In this embodiment a fixed magnet 51 is coupled to the disc. In this fixed magnet case, the rotation would be induced by rotating the cartridge 12 or well 14 within the cartridge. In this fixed magnet embodiment, the motion induced to the disc would be traced directly, with no differencing necessary. In this case the tracked motion could be directly used as the profile trace. Prior to the onset of coagulation there would be no motion coupled and the disc would oscillate uninhibited within the well. With no motion induced, the coagulation profile would be zero. In the fixed magnet case as the coagulation increases, the coupling would increase inducing more motion as coagulation continues. At MA the maximum amount of motion would be induced through the magnet.

Figure 4:
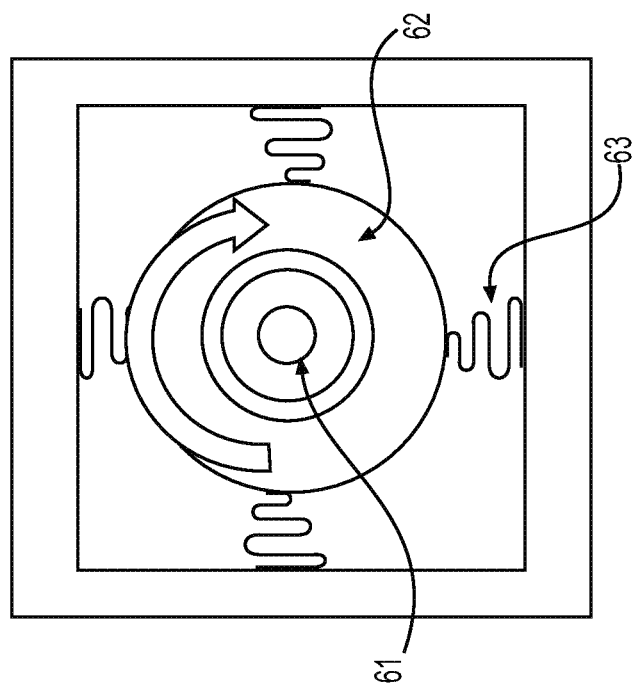
FIG. 4 shows an alternate embodiment with torsion springs.

A third embodiment of a coagulation profiling BioMEMS device is shown FIG. 4. This device has a center disc 61 and an outer ring 62 that is suspended by torsion springs 63. As the blood begins to coagulate, the rotating inner disc 61, actuated via an oscillating magnet, couples to the outer ring 62. This couples a reciprocating motion to the outer ring 2. At MA the maximum amount of motion would be induced through the magnet.

The BioMEMS embodiments shown are not all of the possible variations. For instance, one embodiment could use disc fixed to the center of the well and actuate a ferrous ring in the well. These variation of the described embodiments are apparent to one skilled in the art.

The measurement provided by the invention is impervious to motion. Due to the extremely small dimensions of the BioMEMS device, compared to the conventional size of TEG and ROTEM, the measurement is highly impervious to motion. The small mass of the device and small volume residing in the well present less inertia when external motion is applied. The ability to produce a noise-free measurement in the presence of motion is further enhanced by the magnetic coupling, which fixes the disc and the well in the magnetic field.

Figure 5:
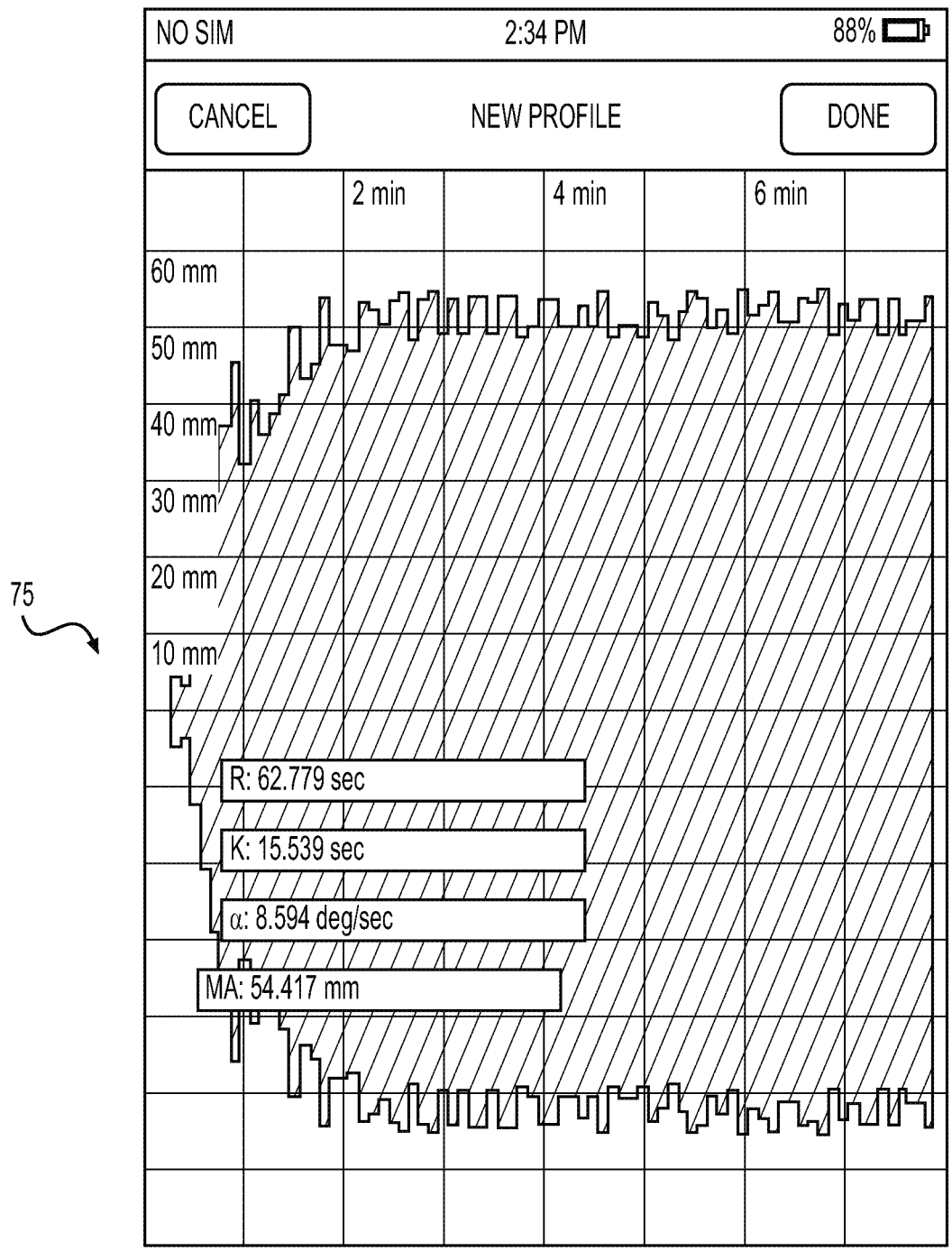
FIG. 5 is an image of a prototype showing accuracy of Level I control fluid.
Figure 6:
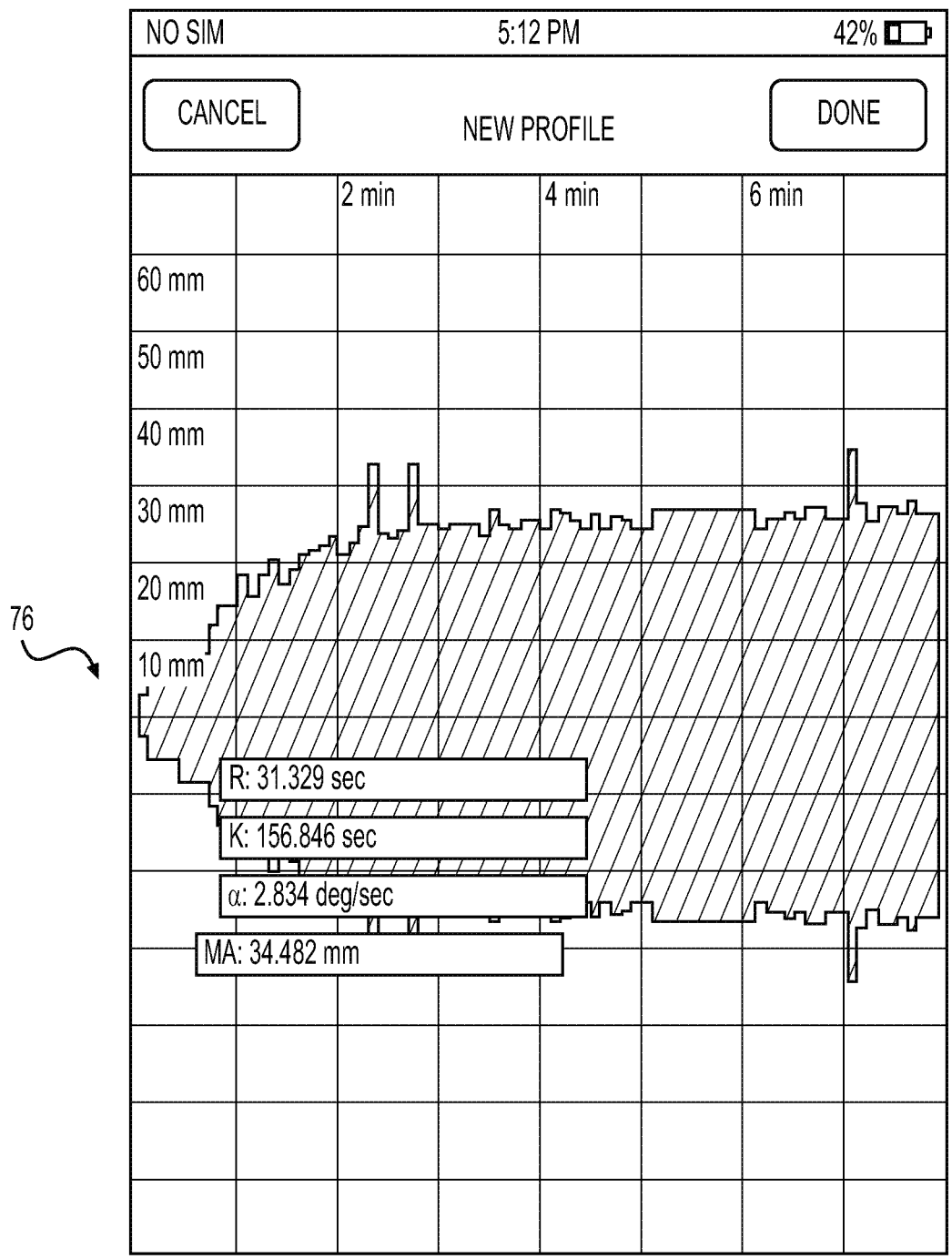
FIG. 6 is an image of a prototype showing accuracy of Level II control fluid.
Figure 7:
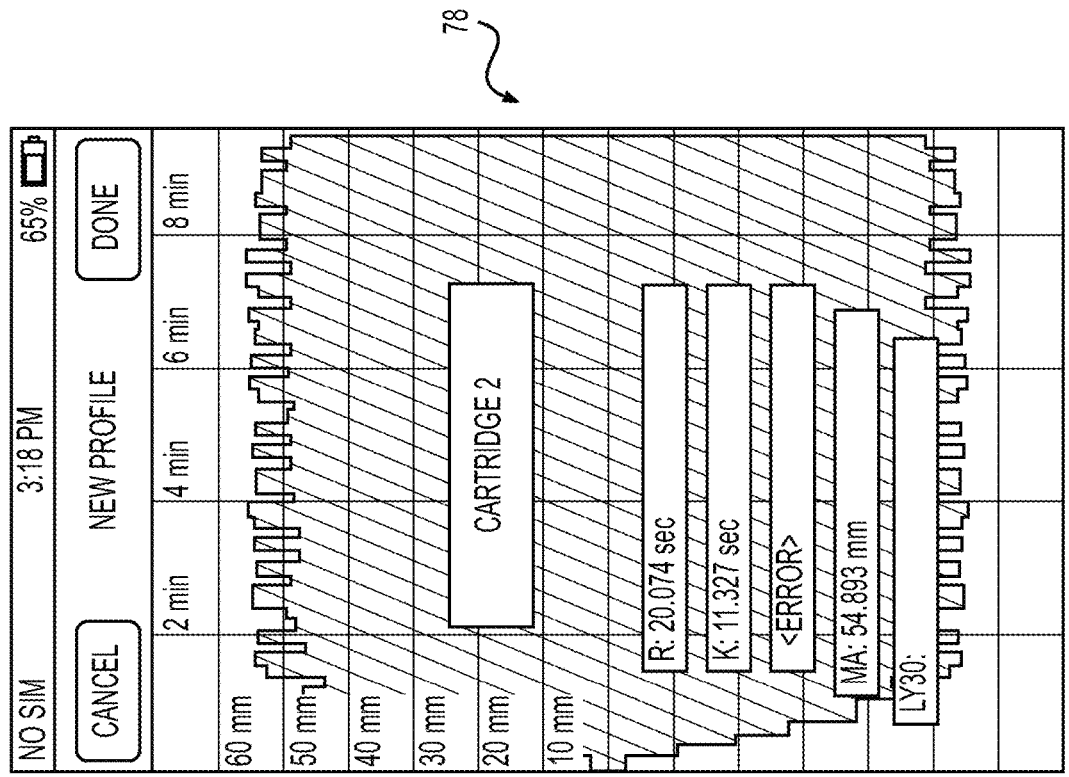
FIG. 7 is an image of a prototype showing repeatability of Level I profiles using two separate cartridges.
Figure 7:
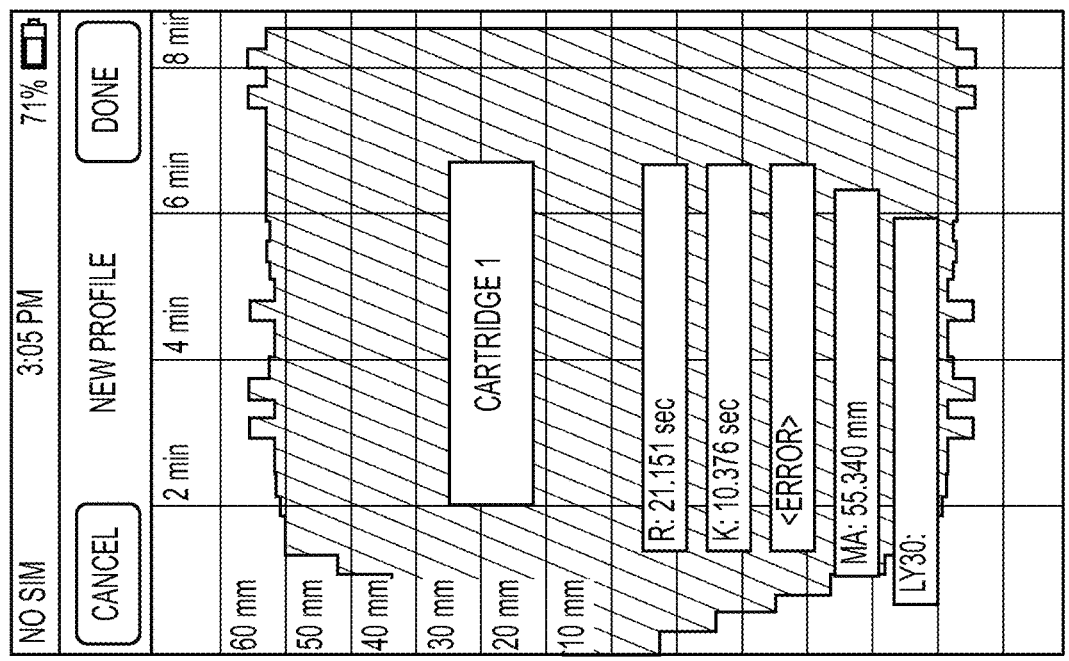
Figure 8:
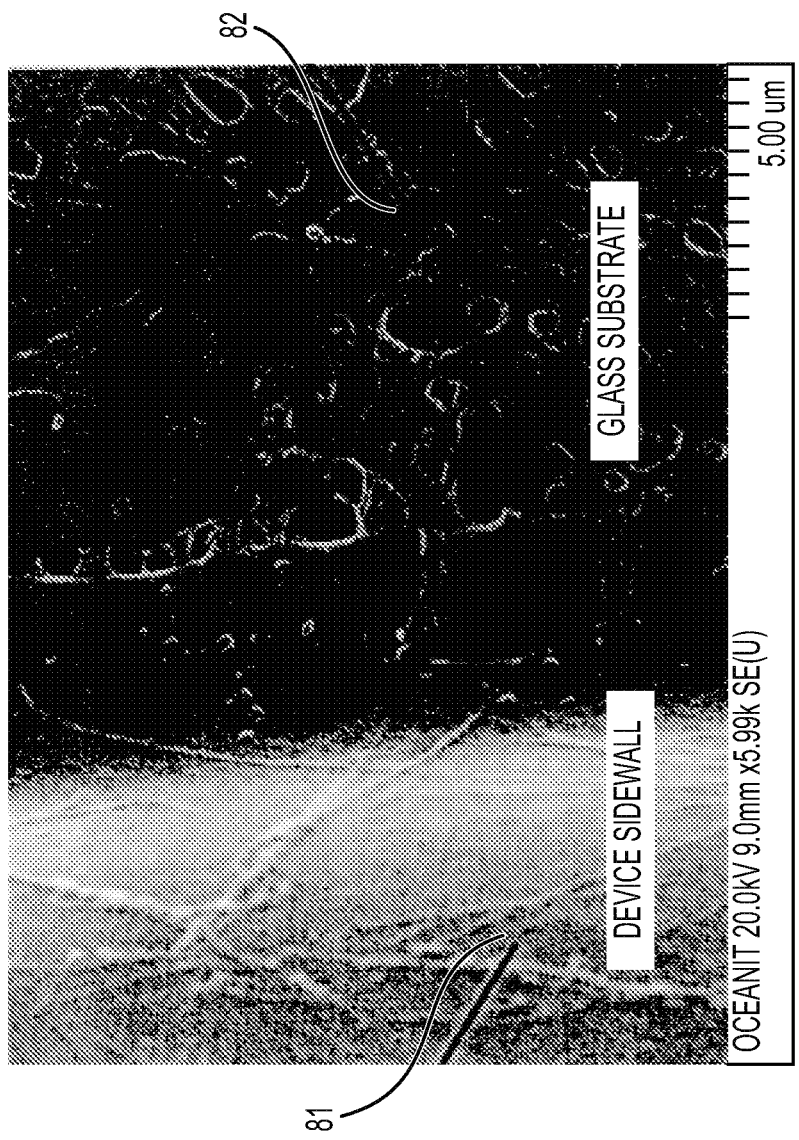
FIG. 8 is an SEM image showing fibrin adhesion into surface of HDDA.

A prototype of the invention has provided concept validation. The image shown in FIG. 1B is an actual working prototype. The coagulation profile on the screen was taken using the prototype and shows the coagulation profile of using a quality control standard used and provided by Haemoscope, the makers of the TEG. The present prototype of the invention has accurately differentiated between the Haemoscope Level 1 control (normal profile) as shown in screen 75 in FIG. 5 and the Level II control (abnormal profile) as shown on screen in FIG. 6. In addition repeatability has been demonstrated with multiple cartridges accurately measuring the samples with nearly identical results, as shown on screens 77 and 78 in FIG. 7. The polymer selection provides improved fibrin adhesion. The use of polymers for the fabrication of the cartridges has also been demonstrated to work well. In addition to being disposable and inexpensive to manufacture, the polymers have demonstrated advantages for us in this invention. Specifically, the use of HDDA promotes fibrinogen to be embedded into the polymer surface prior to the formation of fibrinogen. As the fibrinogen polymerizes it forms an excellent bond to the surfaces. This provides an ideal surface for detecting the viscoelasticity of the coagulating blood between the two HDDA surfaces. FIG. 8 shows fibrin 81 embedded into the surface of a HDDA disc sidewall. FIG. 8 also shows fibrin on the surface of the glass substrate, where air pockets 82 are forming due to a lack of adhesion with no apparent fibrin embedded into the glass surface.

Figure 9:
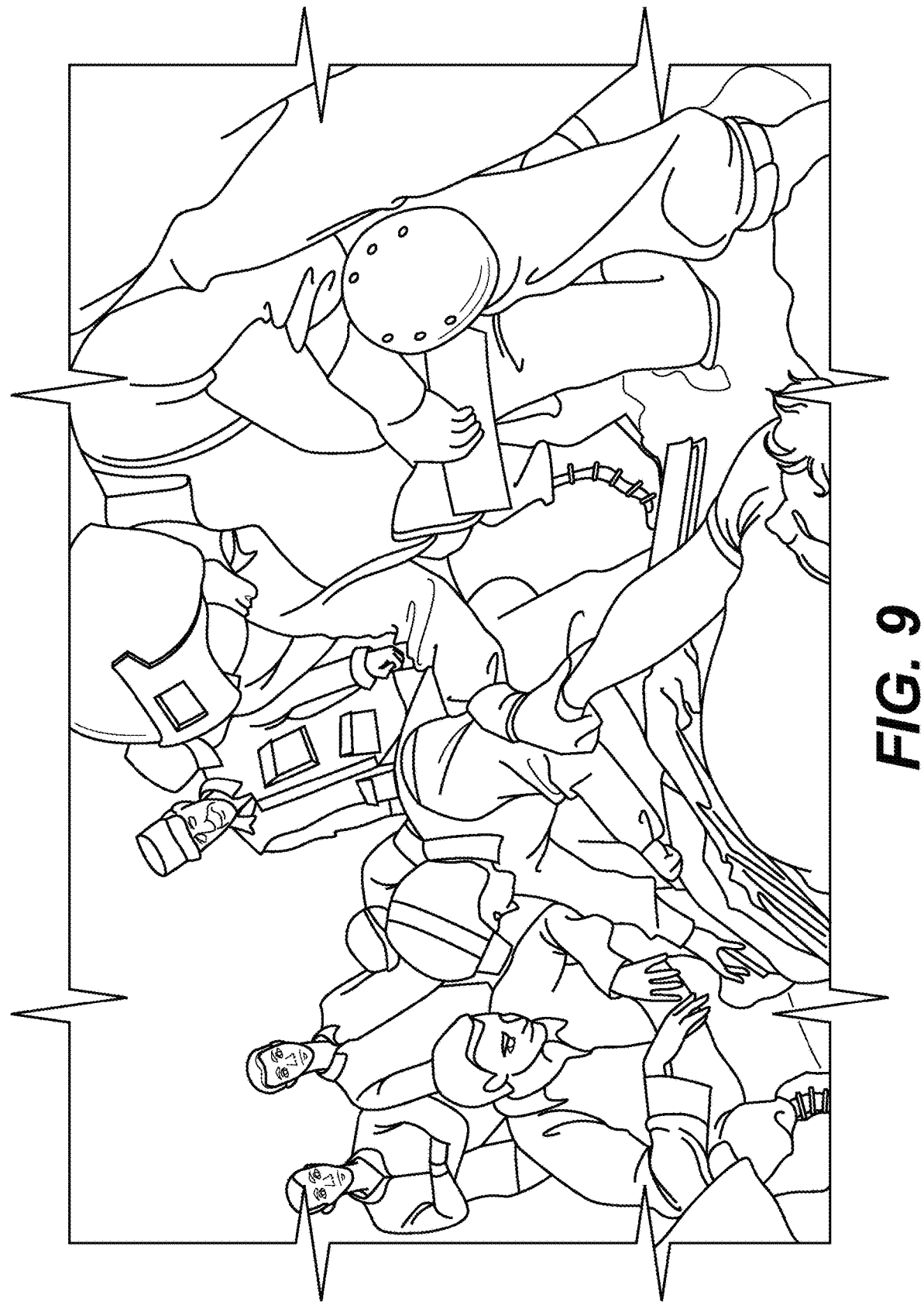
FIG. 9 shows a forward surgical team attending a soldier.

FIG. 9 shows a forward surgical team attending a soldier at a forward position where the present invention is needed, a similar case would be an EMT or paramedic attending a trauma victim.

Figure 10B:
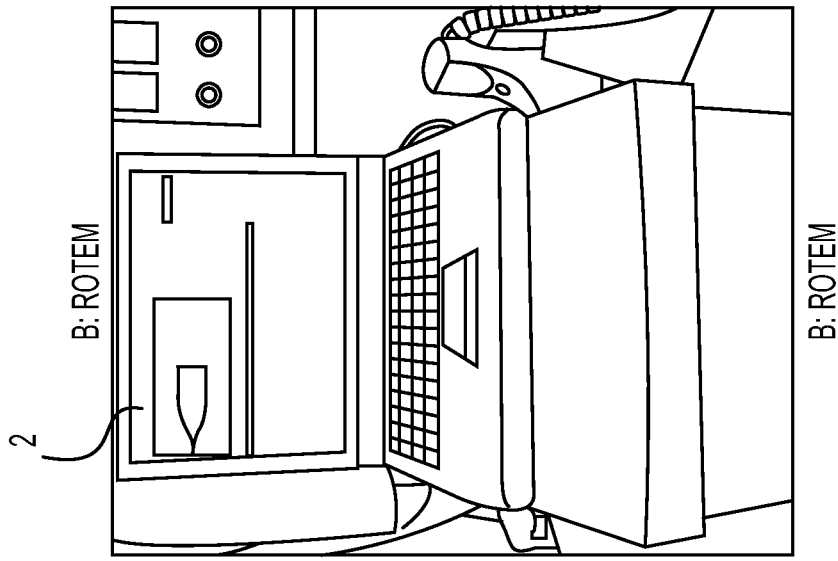
FIGS. 10A and 10B show prior art TEG and ROTEM devices.
Figure 10A:
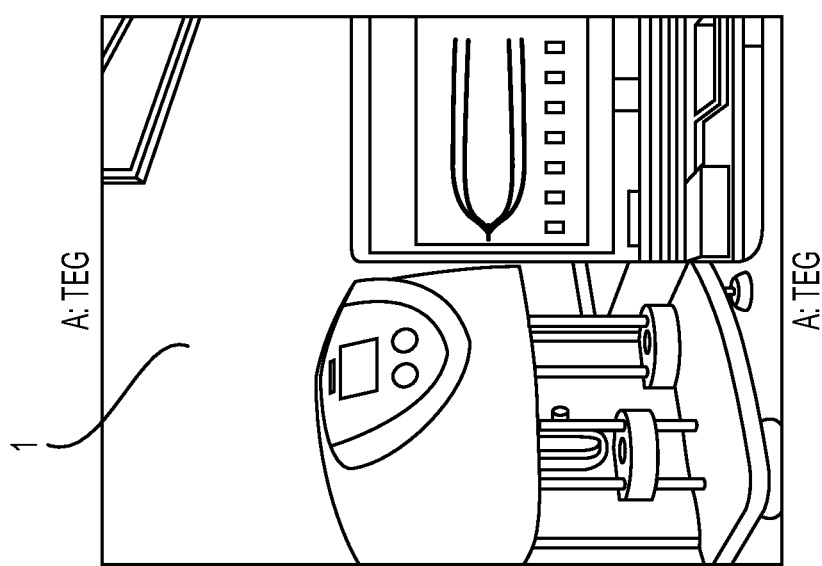

FIGS. 10A and 10B show prior art TEG and ROTEM devices.

Figure 11B:
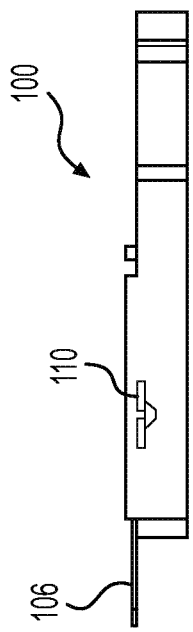
Figure 11A:
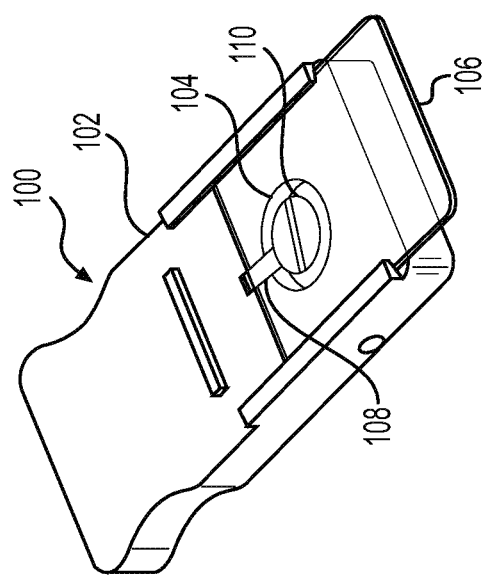

FIGS. 11A and 11B are perspective and a schematic side view showing additional features of the cartridge 100, a platform 102, a well 104, an extended lid 106, an abutment 108 on the platform and a disk 110 attached to the lid 106, all of which are inserted in a receiver before fluid is injected into the well 104. FIG. 11B is a schematic representation of the well 104 and the disk 110 which is attached to a bottom of the lid 106.

Figure 12B:
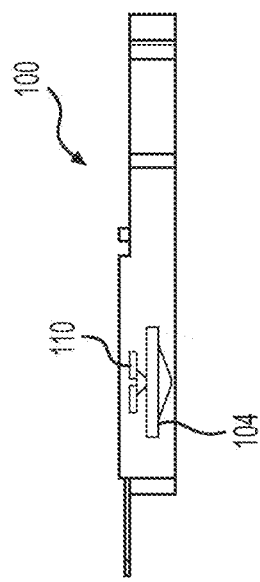
FIGS. 12A and 12B are perspective and a schematic side view showing a cartridge, platform, well, extended lid, an abutment on the platform and a disk attached to the lid. Moving the lid drops the disk into the well after fluid is injected into the well.
Figure 12A:
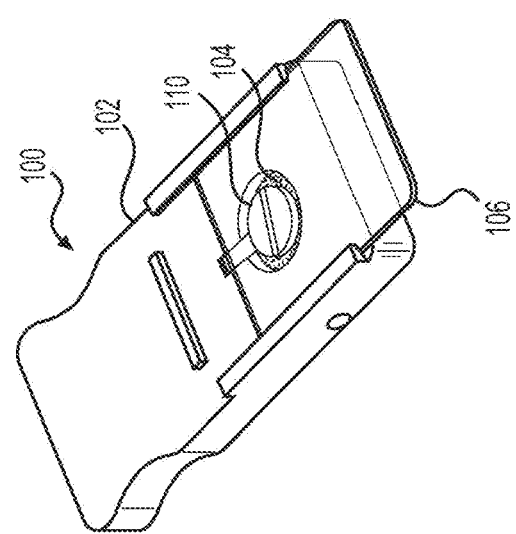

FIGS. 12A and 12B are perspective and a schematic side view showing disk loading technique of the cartridge 100, platform 102, the well 104, the extended lid 106, and an abutment 108 on the platform. Disk 110 is still attached to the lid 106.

Figure 13B:
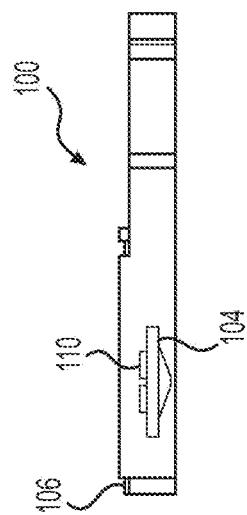
FIGS. 13A and 13B are perspective and a schematic side view showing a cartridge, platform, well, extended cover or lid, an abutment on the platform and a disk attached to the lid, all of which are inserted in a receiver before fluid is injected into the well. After fluid is injected, the lid is pushed back and the disk is dropped from the lid into the well.
Figure 13A:
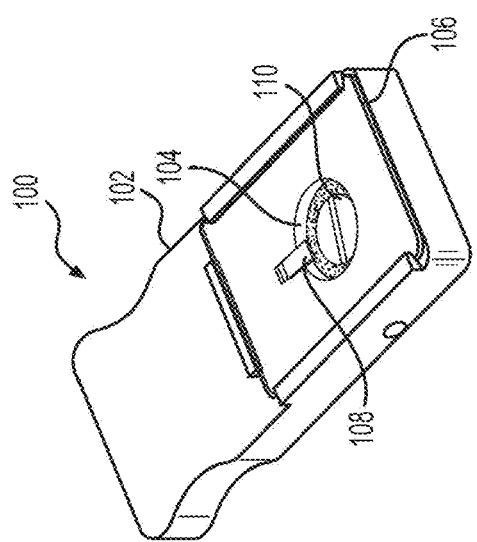

FIGS. 13A and 13B are perspective and a schematic side view showing a cartridge 100, the platform 102, well 104 and lid 106. An abutment 108 on the platform 102 has dislodged disk 110 from the lid after fluid is injected into the well and after lid 106 is pushed back and disk 110 is dislodged and dropped from the lid into the well.

Figure 14:
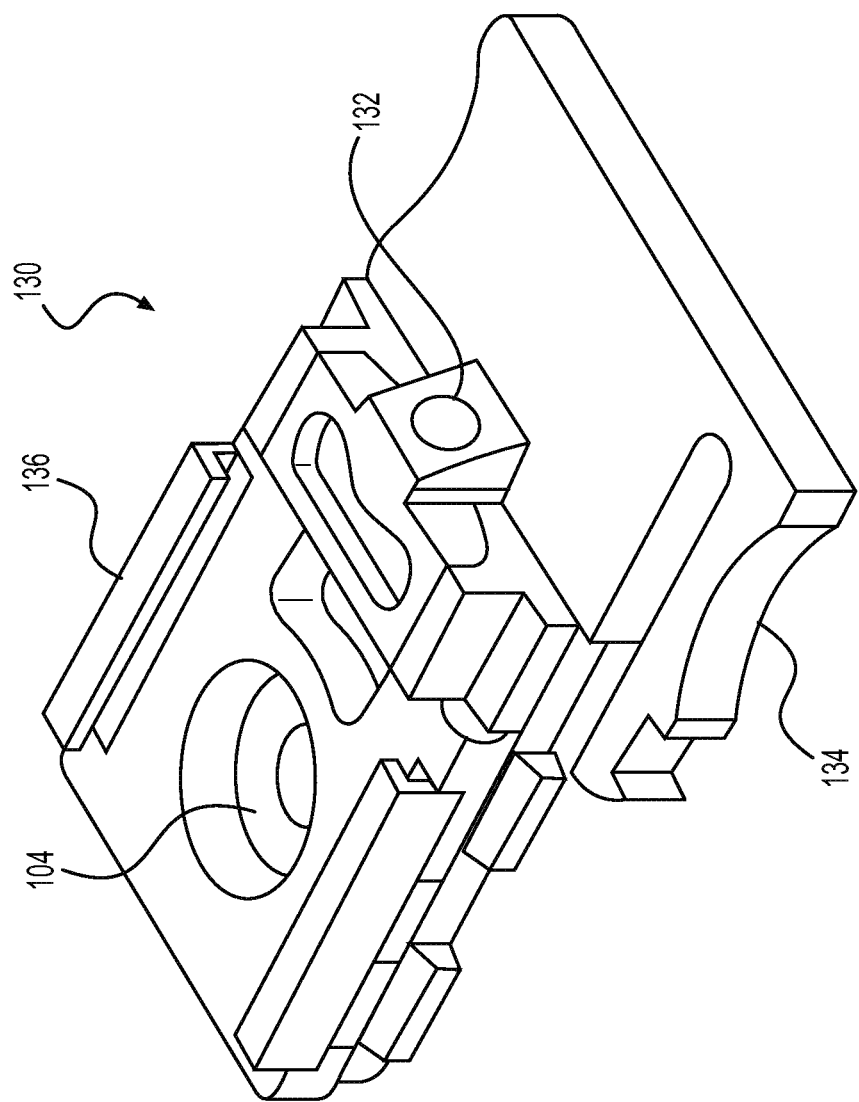

FIG. 14 is a perspective view of a cartridge 130, which shows additional features of an injection port and a retaining clip. In this case it is shown without a lid, showing a fluid injection port 132 at one end of a passageway to the well and retaining clip 134 for retaining the cartridge in the receiver. Upward and inward extending opposite guide rails 136 hold a lid 106, such as in FIGS. 11A-13B.

Figure 15:
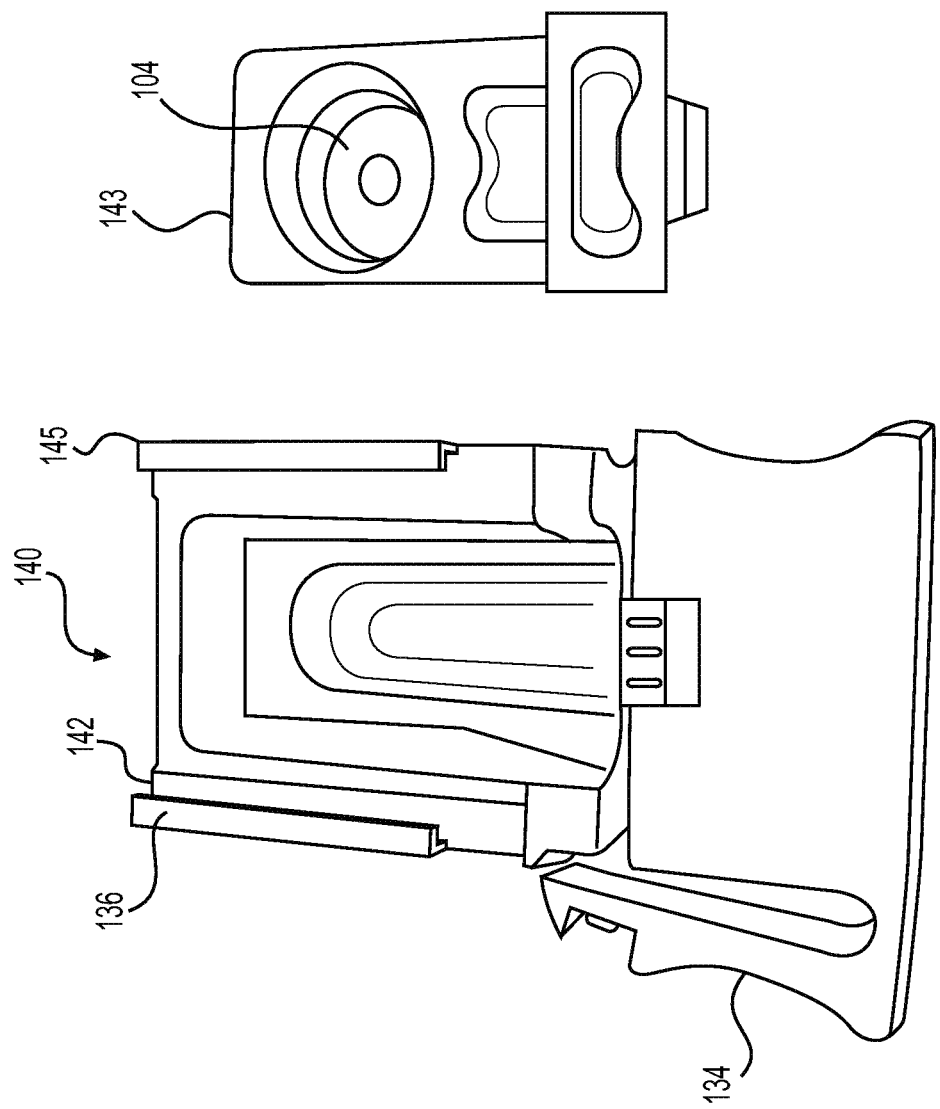

FIG. 15 shows a two-piece injection construction of a cartridge 140 platform 142 for compatibility with manufacture by injection molding. Inner part 143 holds the well 104, and outer part 145 has the retaining clip 134 and the guide rails 136.

Figure 16:
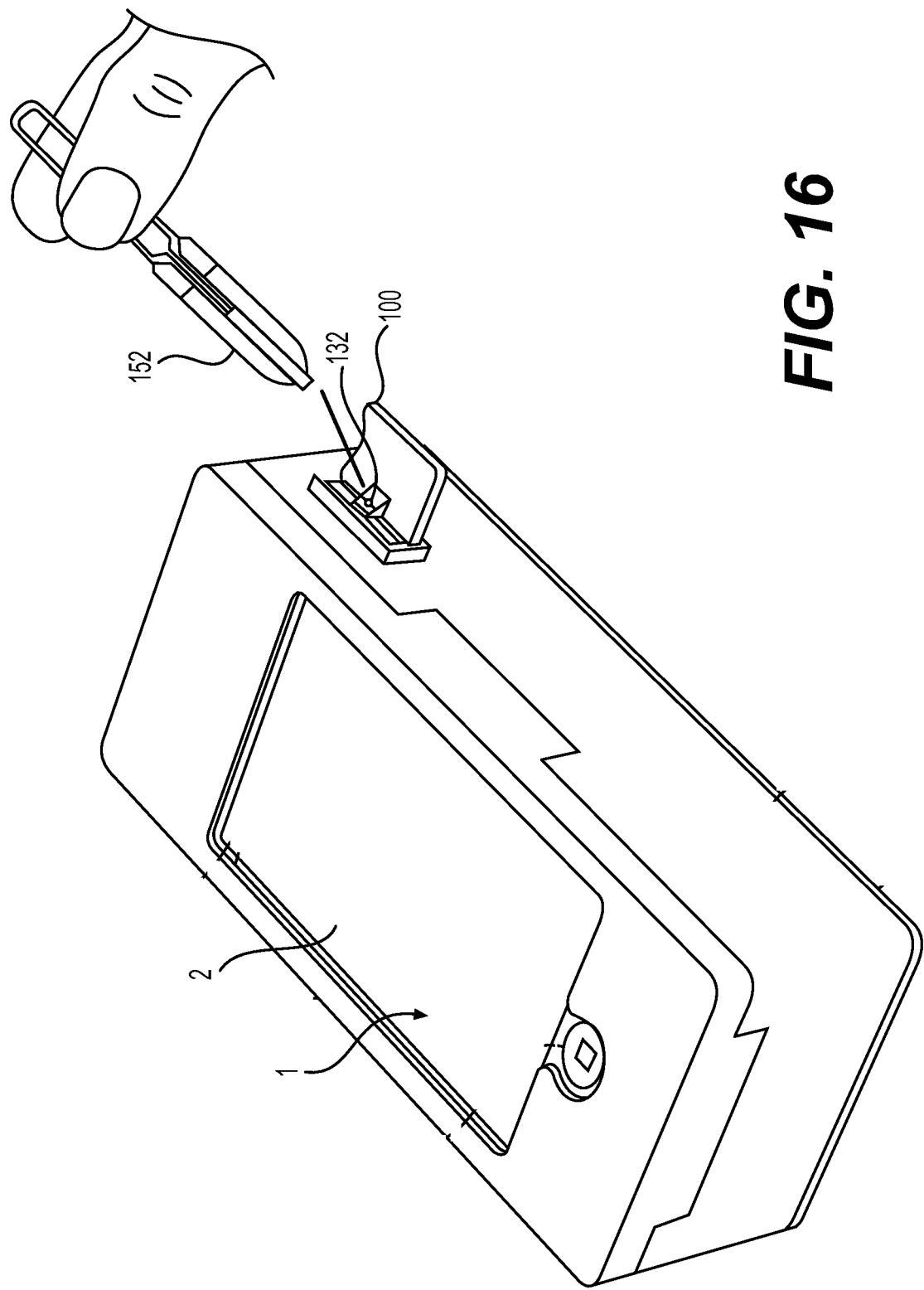
FIG. 16 shows loading protocols and the coagulation profiler with a disposable cartridge inserted and a blood sample ready to be loaded in a port in a portion of the cartridge extended from the case.

FIG. 16 shows loading protocols and the coagulation profiler with a disposable cartridge 100 inserted and a pipette 152 ready to be loaded in a port 132 in a portion of the cartridge extended from the case. Also shown are smartphone 1 with display 2.

Figure 17:
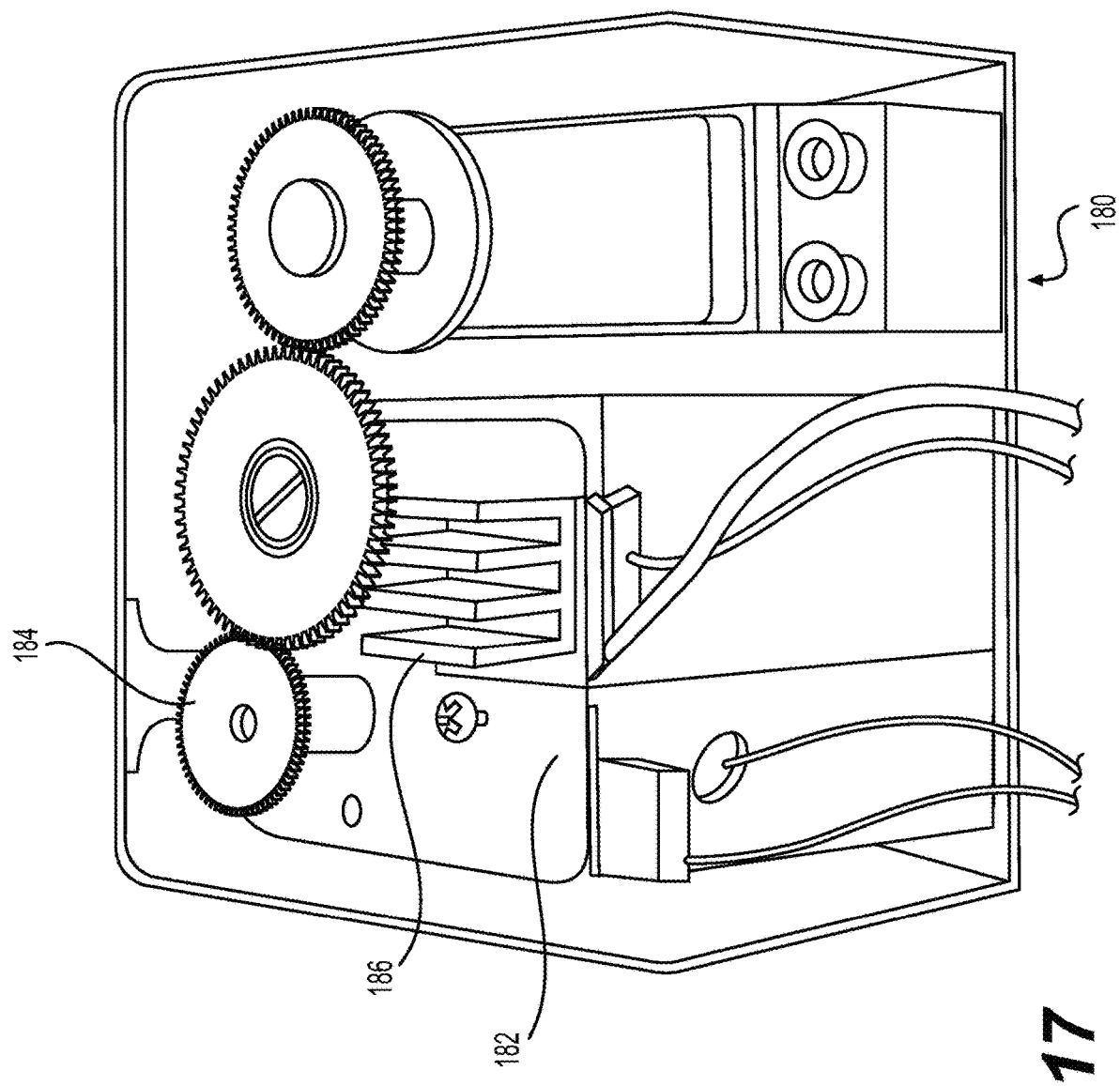
FIG. 17 shows a reciprocating motor with reduction gears and temperature controlling fins mounted on the motor housing.

FIG. 17 shows a reciprocating motor 180 with reduction gears 184 and temperature controlling fins 186 mounted on the motor housing 182.

Figure 18:
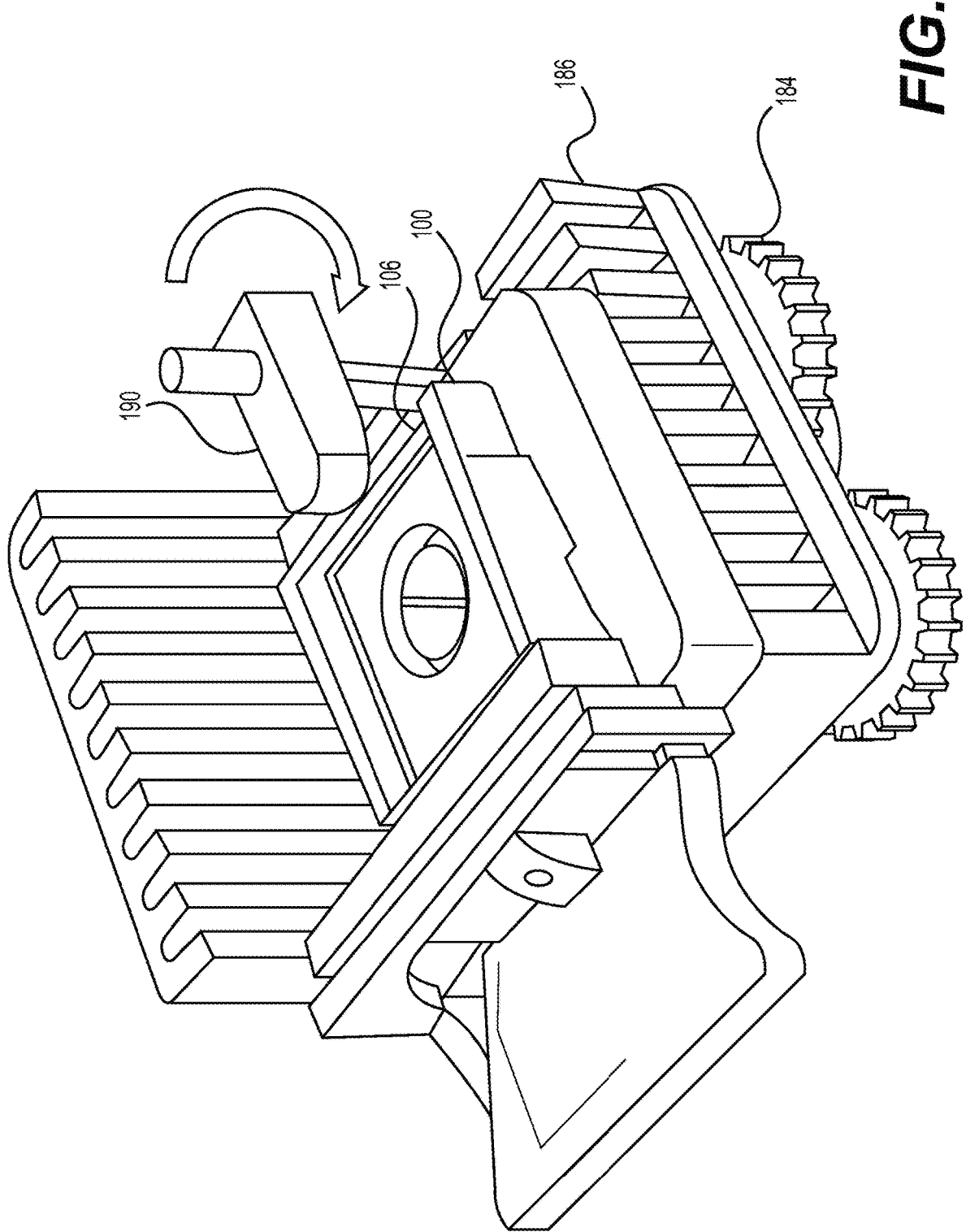
FIG. 18 shows the reduction gearing and extended fins of the temperature controller near the cartridge and a pusher connected to the reduction gears for pushing a lid back onto the cartridge for dislodging and dropping the magnetized disk on blood in the cartridge well.

FIG. 18 shows the reduction gearing 184 and extended fins 186 of the temperature controller near the cartridge 100 and a pusher 190 connected to the reduction gears for pushing a lid 106 back onto the cartridge 100 for dislodging and dropping the magnetized disk on blood in the cartridge well.

While the invention has been described with reference to specific embodiments, modifications and variations of the invention may be constructed without departing from the scope of the invention, which is defined in the following claims.

What is claimed is:

1. A method for measuring coagulation of a sample, comprising:
   activating a measuring device;
   inserting a cartridge into the measuring device;
   placing a liquid sample into a well within the cartridge, the well comprising a disc, the disc comprising a first tracking point comprising a first color, the first tracking point proximate a rotational center of the disc, the disc also comprising a second tracking point comprising a second color spaced apart from the rotational center of the disc, the first color different from the second color;
   activating a magnetic field of the measuring device;
   rotating the disc in a first direction using the magnetic field;
   rotating the disc in a second direction opposite the first direction using the magnetic field;
   illuminating the disc;
   tracking the first tracking point and the second tracking point of the disc with a video camera; and
   calculating changes in movement of the second tracking point with respect to the first tracking point of the disc with a processor to determine coagulation parameters.

2. The method of claim 1, wherein calculating changes in movement of the first tracking point and the second tracking point of the disc occurs in real time.

3. The method of claim 1, wherein the magnetic field comprises a contactless magnetic coupling.

4. The method of claim 1, further comprising displaying the coagulation parameters on a display.

5. The method of claim 1, wherein the display is a smartphone display.

6. The method of claim 1, wherein rotating the disc in a first direction comprises rotating the disc 4° 45' degrees over 10 seconds.

7. The method of claim 1, further comprising controlling an internal temperature in the measuring device.

8. The method of claim 1, wherein the disc further comprises a spindle, such that the disc is spaced apart from a bottom of the well.

9. The method of claim 1, wherein the disc comprises ferromagnetic material to facilitate rotating the disc in the first direction using the magnetic field.

10. The method of claim 1, wherein tracking comprises tracking a reduction in motion of the second tracking point with respect to the first tracking point as the magnetic field becomes no longer strong enough to overcome viscoelasticity of the liquid sample as the liquid sample coagulates.

11. A method for measuring coagulation of a sample, comprising:
   activating a measuring device;
   inserting a cartridge into the measuring device;
   placing a liquid sample into a well within the cartridge, the well comprising a disc, the disc comprising a first tracking point comprising a first color, the first tracking point proximate a rotational center of the disc, the disc also comprising a second tracking point comprising a second color spaced apart from the rotational center of the disc, the first color different from the second color, the disc spaced apart from a bottom of the well via a spindle operably connected to the disc;
   controlling an internal temperature of the measuring device;
   activating a magnetic field of the measuring device;
   rotating the disc in a first direction using the magnetic field;
   rotating the disc in a second direction opposite the first direction using the magnetic field;
   illuminating the disc;
   tracking the first tracking point and the second tracking point of the disc with a camera; and
   calculating changes in movement of the second tracking point with respect to the first tracking point of the disc with a processor to determine coagulation parameters,
   wherein tracking comprises tracking a reduction in motion of the second tracking point with respect to the first tracking point over time as the magnetic field becomes no longer strong enough to overcome viscoelasticity of the liquid sample as the liquid sample coagulates.

12. The method of claim 11, wherein the sample comprises a body fluid sample.

13. The method of claim 12, wherein the sample comprises a blood sample.

14. The method of claim 12, wherein the sample comprises a saliva sample.

15. The method of claim 11, wherein the sample comprises a cervical mucus sample.

16. The method of claim 11, wherein the first color and the second color are fluorescent under UV light.

* * * * *